United States Patent
Hero et al.

(10) Patent No.: US 10,702,291 B2
(45) Date of Patent: Jul. 7, 2020

(54) SYSTEM, GUIDE TOOLS AND DESIGN METHODS RELATED THERETO FOR PERFORMING OSTEOCHONDRAL TRANSPLANTATION SURGERY IN A JOINT

(71) Applicant: EPISURF IP-MANAGEMENT AB, Stockholm (SE)

(72) Inventors: Niklas Hero, Bankeryd (SE); Nina Bake, Lidingö (SE); Jonas Jägerback, Sundbyberg (SE); Katarina Flodström, Danderyd (SE); Emma Widehäll, Taberg (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 202 days.

(21) Appl. No.: 15/740,535

(22) PCT Filed: Dec. 18, 2015

(86) PCT No.: PCT/EP2015/080666
§ 371 (c)(1),
(2) Date: Dec. 28, 2017

(87) PCT Pub. No.: WO2017/001028
PCT Pub. Date: Jan. 5, 2017

(65) Prior Publication Data
US 2018/0185038 A1 Jul. 5, 2018

Related U.S. Application Data

(60) Provisional application No. 62/187,831, filed on Jul. 2, 2015.

(51) Int. Cl.
A61B 17/17 (2006.01)
A61F 2/46 (2006.01)
(Continued)

(52) U.S. Cl.
CPC ...... *A61B 17/1764* (2013.01); *A61B 17/1635* (2013.01); *A61F 2/4618* (2013.01); *A61B 2017/568* (2013.01)

(58) Field of Classification Search
CPC . A61B 17/16; A61B 17/1635; A61B 17/1662; A61B 17/1675; A61B 17/17;
(Continued)

(56) References Cited

U.S. PATENT DOCUMENTS

| | | | |
|---|---|---|---|
| 5,743,916 A | 4/1998 | Greenberg et al. | |
| 8,801,725 B2 * | 8/2014 | Ritter | A61B 17/17 606/102 |

(Continued)

FOREIGN PATENT DOCUMENTS

| | | |
|---|---|---|
| WO | WO-2013/030370 A1 | 3/2013 |
| WO | WO-2013/030372 A1 | 3/2013 |

*Primary Examiner* — Eric S Gibson
(74) *Attorney, Agent, or Firm* — Faegre Drinker Biddle & Reath LLP

(57) ABSTRACT

A system for performing osteochondral transplantation surgery includes a harvesting guide tool for harvesting one or more osteochondral plugs and a transfer guide tool for insertion of each osteochondral plug in a damage site on an articular surface of a joint. A cartilage contact surface of each respective guide tool is adapted to follow the shape of a surface of cartilage or subchondral bone such that they conform to each other. Each respective guide tool includes one or more guide channels adapted to receive a respective surgical tool that slides within the guide channel, and is supported by the guide channel during surgery. The guide channels are configured to harvest and insert a plurality of osteochondral plugs of different sizes. The interiors of the guide channels are provided with markings for marking a rotational position of harvested plugs enabling positioning of the osteochondral plugs at a predetermined angle of rotation.

24 Claims, 28 Drawing Sheets

(51) Int. Cl.
*A61B 17/16* (2006.01)
*A61B 17/56* (2006.01)

(58) Field of Classification Search
CPC ............ A61B 17/1739; A61B 17/1764; A61B 2017/568; A61F 2/4618
See application file for complete search history.

(56) References Cited

U.S. PATENT DOCUMENTS

| | | | | |
|---|---|---|---|---|
| 9,009,012 | B2* | 4/2015 | Bake | A61F 2/30756 703/6 |
| 9,439,678 | B2* | 9/2016 | Bake | A61B 17/1764 |
| 9,468,448 | B2* | 10/2016 | Sikora | A61F 2/3859 |
| 9,826,993 | B2* | 11/2017 | Bake | A61F 2/30756 |
| 9,888,931 | B2* | 2/2018 | Bake | A61F 2/4225 |
| 10,258,353 | B2* | 4/2019 | Sabin | A61B 17/1739 |
| 2003/0100947 | A1* | 5/2003 | Nadler | A61B 17/32053 623/11.11 |
| 2006/0198877 | A1* | 9/2006 | Steinwachs | A61B 17/1635 424/443 |
| 2007/0100459 | A1* | 5/2007 | Rhodes | A61F 2/30721 623/20.19 |
| 2008/0177293 | A1* | 7/2008 | Bharadwaj | A61B 17/1764 606/167 |
| 2008/0243127 | A1* | 10/2008 | Lang | A61B 5/4528 606/87 |
| 2008/0262616 | A1* | 10/2008 | McKay | A61B 17/1635 623/14.12 |
| 2009/0024223 | A1* | 1/2009 | Chen | A61B 17/1604 623/23.63 |
| 2009/0209962 | A1* | 8/2009 | Jamali | A61B 17/1635 606/81 |
| 2010/0121389 | A1* | 5/2010 | Librot | A61B 17/1764 606/86 R |
| 2011/0144648 | A1 | 6/2011 | Gil et al. | |
| 2011/0238071 | A1* | 9/2011 | Fernandez-Scoma | A61C 1/084 606/80 |
| 2013/0172891 | A1* | 7/2013 | Bake | A61F 2/30756 606/80 |
| 2013/0173228 | A1* | 7/2013 | Bake | A61F 2/30756 703/1 |
| 2013/0185927 | A1* | 7/2013 | Bake | A61B 17/1675 29/592 |
| 2014/0142643 | A1* | 5/2014 | Bake | A61B 17/1764 606/86 R |
| 2014/0243836 | A1* | 8/2014 | Bake | A61F 2/30756 606/88 |
| 2014/0249781 | A1* | 9/2014 | Bake | A61F 2/30756 703/1 |
| 2014/0276231 | A1* | 9/2014 | Wood | A61B 17/3205 600/587 |
| 2014/0343403 | A1* | 11/2014 | Kunz | A61B 17/175 600/424 |
| 2015/0105696 | A1* | 4/2015 | Litke | A61F 2/4657 600/587 |
| 2015/0351916 | A1* | 12/2015 | Kosarek | A61F 2/30942 600/407 |
| 2016/0151076 | A1* | 6/2016 | Bake | A61B 17/1604 606/80 |
| 2016/0199075 | A1* | 7/2016 | Bake | A61F 2/4225 606/96 |
| 2017/0100253 | A1* | 4/2017 | Bake | A61B 17/1604 |
| 2018/0185038 | A1* | 7/2018 | Hero | A61F 2/30756 |
| 2019/0076257 | A1* | 3/2019 | Dee | A61F 2/30 |

* cited by examiner

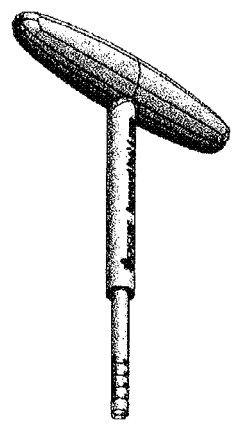
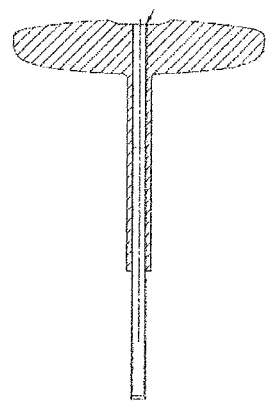
(a) (b)
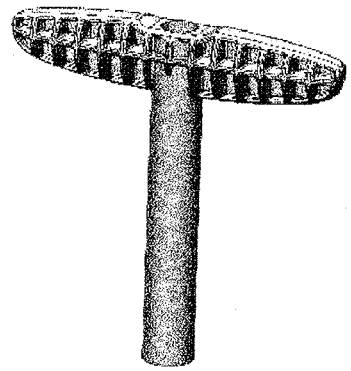
(c) Fig. 8A

SYSTEM, GUIDE TOOLS AND DESIGN METHODS RELATED THERETO FOR PERFORMING OSTEOCHONDRAL TRANSPLANTATION SURGERY IN A JOINT

CROSS-REFERENCE TO PRIOR APPLICATIONS

This application is a § 371 National Stage Application of PCT International Application No. PCT/EP2015/080666 filed Dec. 18, 2015, which claims priority to U.S. Provisional No. 62/187,831 filed on Jul. 2, 2015, both of which are incorporated herein in their entirety.

TECHNICAL FIELD

The present disclosure relates generally to the field of orthopaedic surgery and surgery tools, and especially to a system, guide tools and design methods related thereto for performing osteochondral transplantation surgery in a joint.

BACKGROUND

Pain of the joints of the body is a common problem. One of the most important joint which is liable to wearing and disease is the knee. The knee provides support and mobility and is the largest and strongest joint in the body. Pain in the knee may be caused by for example injury, arthritis or infection. The weight-bearing and articulating surfaces of the knees, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damage, as opposed to other connective tissue, and if healed the durable hyaline cartilage is often replaced by less durable fibro cartilage. This means that damage to the cartilage gradually becomes worse. Along with injury or disease comes the problem with pain, which results in handicap and loss of function. It is therefore important to have efficient means and methods for repairing damaged cartilage in joints, for example in knee joints.

SUMMARY

Various embodiments of a system for performing osteochondral transplantation surgery in a joint are provided. The system comprises a harvesting guide tool, one or more osteochondral plugs, a transfer guide tool for insertion of the one or more osteochondral plug in a damage site on an articular surface of the joint which can be a chondral surface or a trochlear surface. A cartilage contact surface of each respective guide tool is adapted to follow the shape of a surface of a cartilage or subchondral bone in a joint. The cartilage contact surface and the surface of the cartilage or subchondral bone abut each other. Each respective guide tool comprises one or more guide channels adapted to receive a respective surgical tool such that the respective surgical tool slides within the guide channel, and is supported by the guide channel during surgery.

In embodiments herein, each respective guide tool may comprise a plurality of guide channels respectively for harvesting and for transfer of a plurality of osteochondral plugs.

In embodiments herein, the plurality of guide channels and the respective surgical tools may be of different sizes, whereby the plurality of harvested and inserted osteochondral plugs will be of different size.

In embodiments herein, the plurality of osteochondral plugs when inserted may be arranged in a predetermined pattern, whereby the surface of the inserted osteochondral plugs substantially will correspond to the damage site, as it was prior to damage, on the articular surface.

In embodiments herein, each respective guide tool may be individually designed based on patient specific data.

In embodiments herein, each respective guide tool may be provided with pin-holes configured for fastening each respective guide tool to each respective surface of the cartilage or subchondral bone.

In embodiments herein, each respective guide tool may be provided with a stop function adapted to interact with a corresponding stop member provided on each respective surgical tool.

Other embodiments herein relate to a harvesting guide tool for harvesting one or more osteochondral plugs for osteochondral transplantation surgery in a joint. The guide tool comprises a cartilage contact surface adapted to follow the shape of a surface of a cartilage or subchondral bone in a joint from which surface the one or more osteochondral plug is to be harvested, whereby the cartilage contact surface and the surface of the cartilage or subchondral bone conform to each other. The guide tool further comprises one or more guide channels adapted to receive a respective harvesting surgical tool such that the respective harvesting surgical tool slides within the guide channel, and is supported by the guide channel during harvesting surgery.

In embodiments herein, the harvesting guide tool may further comprise a plurality of guide channels for harvesting a plurality of osteochondral plugs.

In embodiments herein, the plurality of guide channels and their respective surgical tools may be of various sizes, whereby the plurality of harvested osteochondral plugs are of various sizes.

In embodiments herein, each guide tool may be individually designed based on patient specific data.

In embodiments herein, each guide tool may be provided with pin-holes configured for fastening the guide tool to the surface of the cartilage or subchondral bone.

In embodiments herein, each guide tool may be provided with a stop function adapted to interact with a corresponding stop member provided on the respective surgical tool.

In other embodiments herein, a transfer guide tool for insertion of one or more osteochondral plug for osteochondral transplantation surgery in a joint is provided. The guide tool comprises a cartilage contact surface adapted to follow the shape of a surface of a cartilage or subchondral bone in a joint into which surface the one or more osteochondral plug is to be inserted, whereby the cartilage contact surface and the surface of the cartilage or subchondral bone conform to each other.

The guide tool further comprises one or more guide channels adapted to receive a respective hole making or insertion surgical tool such that the respective hole making or insertion surgical tool slides within the guide channel, and is supported by the guide channel during transfer surgery.

In embodiments herein, the transfer guide tool may further comprise a plurality of guide channels for insertion of a plurality of osteochondral plugs.

In embodiments herein, the plurality of guide channels and their respective surgical tool may be of various sizes, whereby the plurality of inserted osteochondral plugs will be of various sizes.

In embodiments herein, the guide tool may be individually designed based on patient specific data.

In embodiments herein, the guide tool may be provided with pin-holes configured for fastening the guide tool to the surface of the cartilage or subchondral bone.

In embodiments herein, the guide tool may be provided with a stop function adapted to interact with a corresponding stop member provided on the surgical tool.

In embodiments herein, the transfer guide tool may further comprise one or more detachably attached guide channel inserts adapted to fit inside the one or more guide channels, and adapted to receive a respective surgical tool, by which tool damaged matter is removed from the damage site.

In embodiments herein, the one or more guide channels may be adapted to position the one or more osteochondral plug in a predetermined angle of rotation. In other embodiments herein, a method of designing a system for performing osteochondral transplantation surgery in a joint is provided. The system comprises a harvesting guide tool, one or more osteochondral plugs, and a transfer guide tool for insertion of the one or more osteochondral plugs in a damage site on an articular surface of the joint. The method comprises determining physical parameters for the damage site in the joint based on obtained image data, generating, based on the determined physical parameters, design parameters for the one or more osteochondral plugs to fit the damage site, wherein the design parameters comprise at least the number of, the size of, and the relative placement of, the one or more osteochondral plugs, selecting, based on the determined physical parameters, at least one healthy surface of the joint substantially aligning with the surface of the cartilage damage site, from at least one healthy surface the one or more osteochondral plugs is to be harvested, generating, based on the generated design parameters for the one or more osteochondral plugs, design parameters for each of the respective guide tool.

The scope of embodiments herein is defined by the claims, which are incorporated into this section by reference. A more complete understanding of embodiments of embodiments herein will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

They will be described in the following with reference to non-limiting examples with reference to the accompanying drawings, of which:

FIG. 8a shows different aspects of a hole-maker removal tool.

Embodiments of the present disclosure and their advantages are best understood by referring to the detailed description that follows. It should be appreciated that like reference numerals are used to identify like elements illustrated in one or more of the figures.

DETAILED DESCRIPTION

Figure 1:
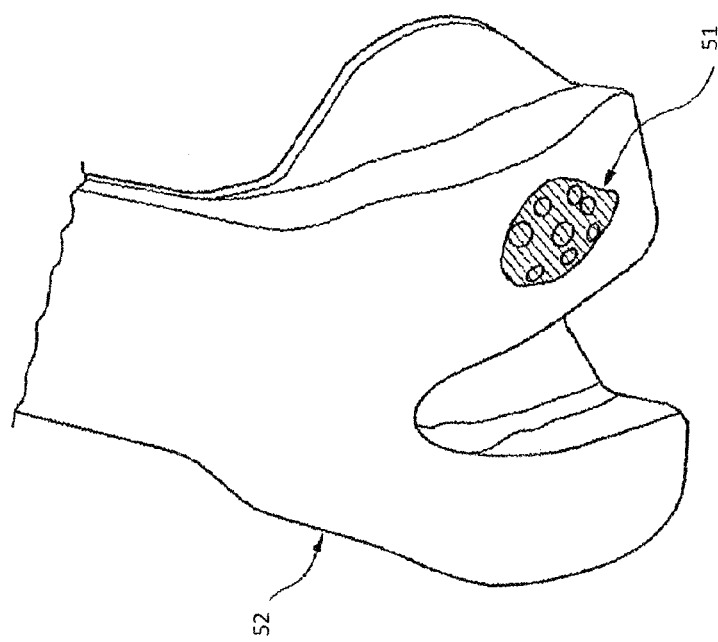
FIG. 1 shows a damaged distal end of a left femur.

Embodiments described herein relate to the field of treatment of lesions through osteochondral transplantation.

The lesions may be cartilage or bone lesions, or combined bone and cartilage lesions, which may be treated by use of a cartilage and bone portion.

Further, examples of guide tools and tools that facilitate such procedures will be described.

Further embodiments herein relate to a design method for design of a system and of guide tools. Examples of surgery kits, kits of tools and methods for performing an osteochondral transfer to treat lesions of an articular surface of a joint will further be described.

In order to better appreciate embodiments herein, a discussion regarding prior art and problems related thereto will be provided in the following.

Today's knee prostheses are successful in relieving pain but there is a limit to the lifetime of the prostheses to 10-20 years. The surgical operation is demanding and the convalescence time is long. In many cases today, surgery is avoided if physiotherapy and painkillers can reduce the pain. Prostheses are therefore primarily for elderly patients in great pain, at the end of the disease process with a totally destroyed joint. There are different kinds of prostheses, such as unicompartmental prostheses, total prostheses and revision knees, the latter being used after a prosthesis failure.

Other attempts, not using prostheses, are practiced at various clinics around the world with the main objective of repairing or rebuilding damaged cartilage and the underlying bone. These include biological approaches such as microfracturing, cartilage cell transplantation, and osteochondral transplantation with autografts or allografts. As a complement to biological approaches there are also metal implants, both patient-specific and "off the shelf", available on the market, for the treatment of focal chondral and osteochondral lesions.

In the surgical operation of repairing cartilage and bone tissue using transplants or implants it is critical that the repair object, for example an implant or a transplant, for example a healthy cartilage and bone plug, be positioned in a precise manner. If the repair object is offset from its intended position it may cause increased wear or load on the joint. For example, if the repair object is tilted, this may result in an edge that projects above the cartilage surface and causes wear on the opposing cartilage in the joint. Another example is when the repair object is placed in a position with the surface of the repair object projecting above the surface of the cartilage causing the joint to articulate in an uneven manner and increasing the load on an opposing point of the joint. For the patient, also small misplacements or deviations from an ideal position may result in pain, longer convalescence time or even a surgical operation being done in vain and making it more difficult to repair the damage in the joint.

Implantation of healthy cartilage and bone 'plugs' into damaged cartilage and bone areas is especially advantageous for young patients who are still growing, with better cartilage self-repair capacity than adults. The plugs are also referred to as grafts. Moving cylindrical plugs of cartilage and underlying bone from areas not exposed to heavy loads to damaged areas is often referred to as osteochondral autograft transplantation or mosaicplasty. The plugs are each a few millimeters in diameter, and when multiple plugs are moved into a damaged area the result is a surface with mosaic tile appearance. Osteochondral autograft transfer system, OATS®, Arthrex Inc., is a technique very similar to mosaicplasty but during the OATS procedure the plugs are usually larger, and therefore only one or two plugs are needed to fill the area of cartilage damage. Because of this it does not take on the mosaic appearance, but the principle is the same.

Today mosaicplasty or osteochondral autograft transfer is performed using a graft harvesting tool, which harvests the osteochondral plug in a desired size. A hole is created in the cartilage and underlying bone at the site of the lesion. After the osteochondral plug is collected the plug is then placed in the recipient hole by using a plunger which is a part of the harvesting tool. These tools are not easy to use and a large burden is therefore placed on the surgeon in order not to misplace or misfit the implant.

Plugs well supported by healthy bone and cartilage heal well, but unsupported grafts tend to recede and can become covered by fibrous tissue. It is therefore important that the implanted plugs are correctly sized and the graft is seated in a well-supported recipient site. It is also important to harvest the plugs from suitable sites where the surface bears as little load as possible, the bone and cartilage are of good quality and the surface curvature is matches the curvature of the recipient site as much as possible.

Today there are known guide tools which may assist in placement of single implants or single transplants.

Examples of prior art disclosing tools for replacement of damaged bone and/or cartilage using mosaicplasty or osteochondral autograft transfer, OATS, or other similar methods where the damaged cartilage and bone are replaced with healthy cartilage and bone are described in the following prior art documents.

EP 2 514 373 B1 describes a guide tool intended for insertion of cartilage and bone plugs, where the guide tool comprises at least two guide channels and a cartilage contact surface.

WO 2012/143531 A1 describes a design method for designing a guide tool for cartilage repair, including selecting repair objects to fit the individual cartilage damage site, where the repair objects have surfaces intended to align with the articular cartilage surface in the joint, based on the healthy surface contour curvature.

WO 2009/108591 A1 describes a method of repairing an articular cartilage defect including use of a drill guide guiding drill holes in different angles into the bone.

U.S. Pat. No. 8,998,918 B2 describes a device and a technique for preparation and implantation of large osteochondral allografts, up to 40 mm in diameter, for resurfacing of a human joint with precise surface matching of the donor and recipient. The technique involves use of a guide comprising an inner guide and an outer guide wherein the articular surface of the guide matches the articular surface of both the allograft and the recipient site. The guides can be prepared in such a way that they exactly match a variety of contours of the articular geometry of a specified joint, and it is described how this is performed.

U.S. Pat. No. 6,488,033 describe a method of obtaining and placing an osteochondral allograft in substantially the same orientation as the damaged segment of the bone which is initially removed from the patient. The placement of the guides is essentially dependent on free hand techniques and the guides do not provide a precise match with the contours of the cartilaginous surface.

U.S. Pat. No. 6,591,581 describe a method and instrumentation for the preparation, distribution and insertion of cylindrical, size specific osteochondral allografts.

U.S. Pat. No. 6,591,581 describes a method for preparing and inserting round, size specific osteochondral allograft cores in the knee, comprising the step of placing an order for a pre-cut allograft core and delivering the pre-cut allograft core. To harvest the donor core, a coring trephine with teeth is preferably used. Alternatively, a donor harvester having a straight cutting edge as described in U.S. Pat. No. 5,919,196, EP 0 824 893 B1 and U.S. Pat. No. 6,592,588 can be used. Those patents describe a method and apparatus for osteochondral autograft transplantation, describing harvesting and insertion of osteochondral core/plugs in a joint.

U.S. Pat. No. 8,109,935 describes an implant inserter device comprising a pushrod slidable received within an outer collar of the device, which may be used to place an implant in a damaged cartilage area. A guide wire is used to guide a lesion gauge (mounted on the guide wire) in position for removal of damaged cartilage and bone.

US2005/0137600 A1 and EP 1 980 216 B1 describe a technique and instruments for repair of articulate cartilage in joints. For example an implant delivery device is described, acting both as a cartilage cutter and a guide.

WO2006/060416 A2 describes devices and a method for cartilage repair wherein the devices comprise a drill guide having a proximal end shaped and conformed to the shape of the tissue at the perimeter of the defect.

U.S. Pat. No. 8,608,748 describe a device for an orthopaedic knee procedure. The device can include a drill guide. The device includes two guides, an alignment guide with a body with an inner anatomically-engaging surface shaped to closely conform and mate with a corresponding tibia joint surface and a drill guide wherein the alignment guide is mounted on the tibial joint surface and the drill guide is mounted on the alignment guide. The guides are made from a pre-operative plan formed from an MRI or CT scan of the patient and rely on matching subcutaneous anatomic feature for correct positioning. The guide described is not intended for small cartilage damage repair or for guiding placement of implants. It is a guide for drilling before fastening larger implants.

The solutions described in the prior art above destroy more of the original cartilage in a patient than necessary. There is no way to make sure the harvested plugs are of suitable quality and have suitable surface curvature for autograft transplantation. Therefore, there is a need for further improved solutions making possible a more accurate transplantation procedure and improved transplantation results. There is also a need for methods that facilitate successful performance of an osteochondral transplantation procedure.

An object of embodiments herein is therefore to provide means for enabling improved precision of the insertion and positioning of cartilage and bone plugs at an articular surface of a joint.

Embodiments herein aim to at least in part solve problems during bone transplantation procedures such as mosaicplasty or osteochondral autograft thansfer, OATS.

Embodiments herein relate to a system and to guide tools for use in orthopaedic surgery.

The system may be used during osteochondral transplantation such as mosaicplasty or osteochondral autograft transfer, OATS. The transfer guide may further be used during implantation of implants. The guide tools according to embodiments herein guide the use of different surgical tools used during cartilage or bone repair surgery. The surgical tools or insert tools may be used inside the guide tools and are thereby supported by the guide tool during surgery.

A system for performing osteochondral transplantation surgery in a joint 50 will now be described in detail with reference to FIGS. 1-27.

The system may be used for both autograft and allograft transplantation. Two different, or identical, guide tools 100, 200 are comprised in exemplified embodiments herein; a harvesting guide tool 100 for harvesting of osteochondral plugs and a transfer guide tool 200 for insertion of repair objects such as osteochondral plugs to repair a bone and/or cartilage lesion of a joint 50. Any of the exemplified guide tools may be individually designed based on patient specific data. Further, any of the exemplified guide tools may be provided with pin-holes by which the guide tool is fastened to the surface of the cartilage or subchondral bone. The system comprises a first guide tool 100 for harvesting one or more osteochondral plugs and a second guide tool 200 for insertion of the one or more osteochondral plug in a damage site on an articular surface of the joint 50. The damage site may be a bone and/or cartilage damage site. A cartilage contact surface 110 of each respective guide tool 100, 200 is adapted to follow the shape of a surface of a cartilage or subchondral bone in a joint 50. The cartilage contact surface 110 and the surface of the cartilage or subchondral bone abut each other. Each respective guide tool 100, 200 comprises one or more guide channels 130 adapted to receive a respective surgical tool, in such a way that the respective surgical tool slides within the guide channel 130, and is supported by the guide channel 130 during surgery. Each respective guide tool 100, 200 in the system may comprise a plurality of guide channels 130 for harvesting and for insertion, respectively, of a plurality of osteochondral plugs.

The guide channels 130 and the respective surgical tools may be of different sizes, whereby the harvested and inserted osteochondral plugs will be of different size. The osteochondral plugs may, when inserted, be arranged in a predetermined pattern. Thereby, the surface of the inserted osteochondral plugs will substantially correspond to the cartilage damage site on the articular surface. Each respective guide tool comprised in the system may be individually designed based on patient specific data. Further, each respective guide tool 100, 200 may be provided with pin-holes configured for fastening each respective guide tool to each respective surface of the cartilage or subchondral bone. Still further, each respective guide tool may be provided with a stop function adapted to interact with a corresponding stop member provided on each respective surgical tool. The system may be used for replacing a portion, e.g. a diseased area or an area slightly larger or smaller than a diseased area, of a joint 50, comprised of cartilage and/or bone, with a cartilage repair object using a guide tool which enables the surgeon to place the cartilage repair objects in near anatomic fit with the surrounding structures and tissues. The cartilage harvesting and insert tools 100, 200 may comprise different parts, for example a harvesting tube, a plunger, an insert adapter and a depth control tool. Further the plug harvesting and insertion tools 100, 200 may comprise a depth control function. The plug harvesting and insert tools 100, 200 may also be equipped with a plunger used for ejection of the harvested cartilage and bone plug into the damaged cartilage area or into an insertion adapter. In one embodiment the plug harvesting tool and the inserting tool are one and the same tool, while in another embodiment the plug harvesting tool and the inserting tool are two different tools.

FIG. 1 shows the distal end of a femur 52 with an example of a condylar damage site 51, shown as a cartilage repair site, treated according to methods of embodiments herein. For example, a transfer guide tool 200 according to embodiments herein may be used.

A transplantation procedure, which is intended to relieve pain and prevent further joint degeneration, involves selecting donor sites for osteochondral plugs, capped with intact cartilage. Donor sites are selected along non weight-bearing areas of the femoral condyles or the trochlea. Multiple osteochondral plugs can be harvested and transplanted depending on the size and nature of the lesion and the anatomy of the patient's knee, as well as of the preference of the surgeon. Recipient repair sites typically are located on the weight-bearing area of the medial and lateral femoral condyles. Other possible repair sites are in the knee trochlear grove or in other joints such as the ankle, elbow or hip.

Figure 2:
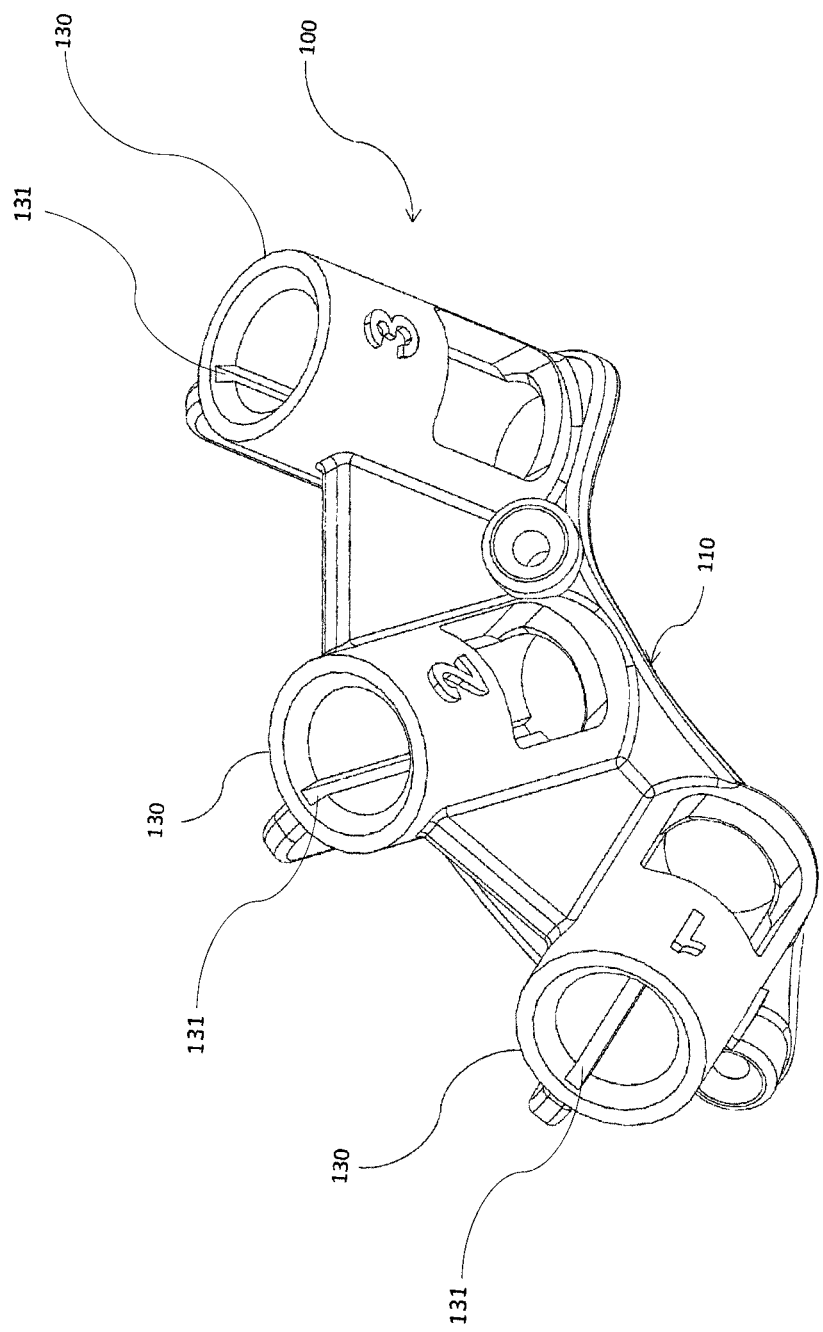
FIGS. 2 and 3 show two different perspective views of one embodiment of a harvesting guide tool.

FIG. 2 shows an example of a harvesting guide tool 100 for harvesting one or more osteochondral plugs for osteochondral transplantation surgery in a joint 50 (not shown). The guide tool 100 comprises a cartilage contact surface 110 adapted to follow the shape of a surface of a cartilage or subchondral bone in a joint 50 (not shown) from which surface the one or more osteochondral plug is to be harvested. The cartilage contact surface 110 and the surface of the cartilage or subchondral bone abuts each other. The guide tool 100 further comprises one or more guide channels 130. In the exemplified embodiment three guide channels 130 are provided. The guide channels 130 are adapted to receive a respective harvesting surgical tool such that the respective harvesting surgical tool slides within the guide channel, and is supported by the guide channel 130 during harvesting surgery. The guide tool 100 for harvesting may further comprise a plurality of guide channels for harvesting a plurality of osteochondral plugs. The guide channels 130 and the respective surgical tool (not shown) may be of different sizes, whereby the plurality of harvested osteochondral plugs will be of different size. The guide tool 100 may be individually designed based on patient specific data. Further, the guide tool 100 may be provided with pin-holes configured for fastening the guide tool 100 to the surface of the cartilage or subchondral bone. The guide tool may further be provided with a stop function adapted to interact with a corresponding stop member provided on the surgical tool. The guide tools may be designed allowing repair objects to be harvested in a non weight-bearing part of the joint 50 and at the same time allowing placement of the repair objects in the damaged site in the joint 50. The guiding will further help selecting the proper spacing between multiple plugs, so the depth of one harvested plug does not intersect with an adjacent harvested plug. Proper pre-planning of the harvesting surgery will ensure that the harvesting is performed on a site where the cartilage and bone are of good quality. The harvesting guide tool 100 may further facilitate marking of the rotation of a plug by marking means 131, so matching of the curvature of the harvested plug may be done in the best possible way with the curvature of the insertion site. The combination of the harvesting guide tool 100 and a suitable harvesting tool may help to obtain the desired depth of the harvested plug as the harvesting tool may have a stop function when it is used together with the harvesting guide. The harvesting guide tool 100 may be designed to be used for harvesting one or more osteochondral plugs. The plugs may be size-specific.

Figure 3:
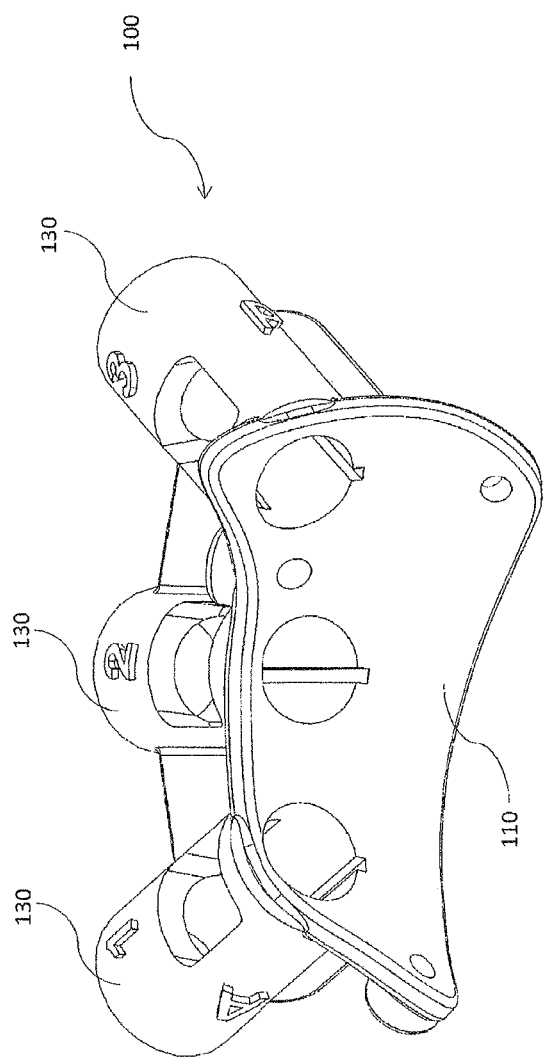

FIG. 3 shows another perspective view of an exemplified harvesting guide 100, showing three guide channels 130 for plug harvesting and a cartilage contact surface 110.

Figure 21:
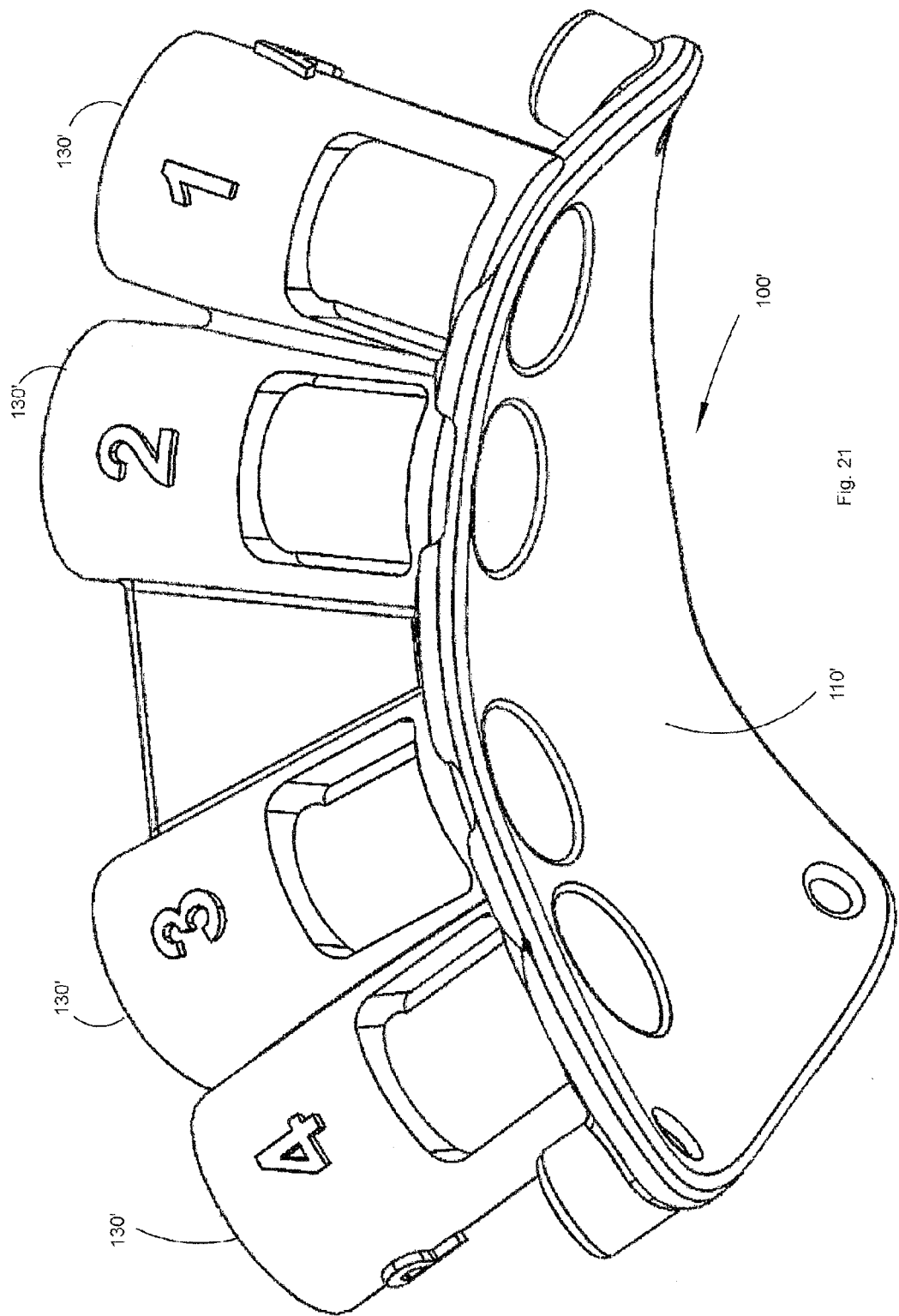
FIGS. 21 and 22 show two different views of another embodiment of a harvesting guide tool, such as that shown in FIGS. 2 and 3, but with four guide channels instead of three for harvesting plugs.
Figure 22:
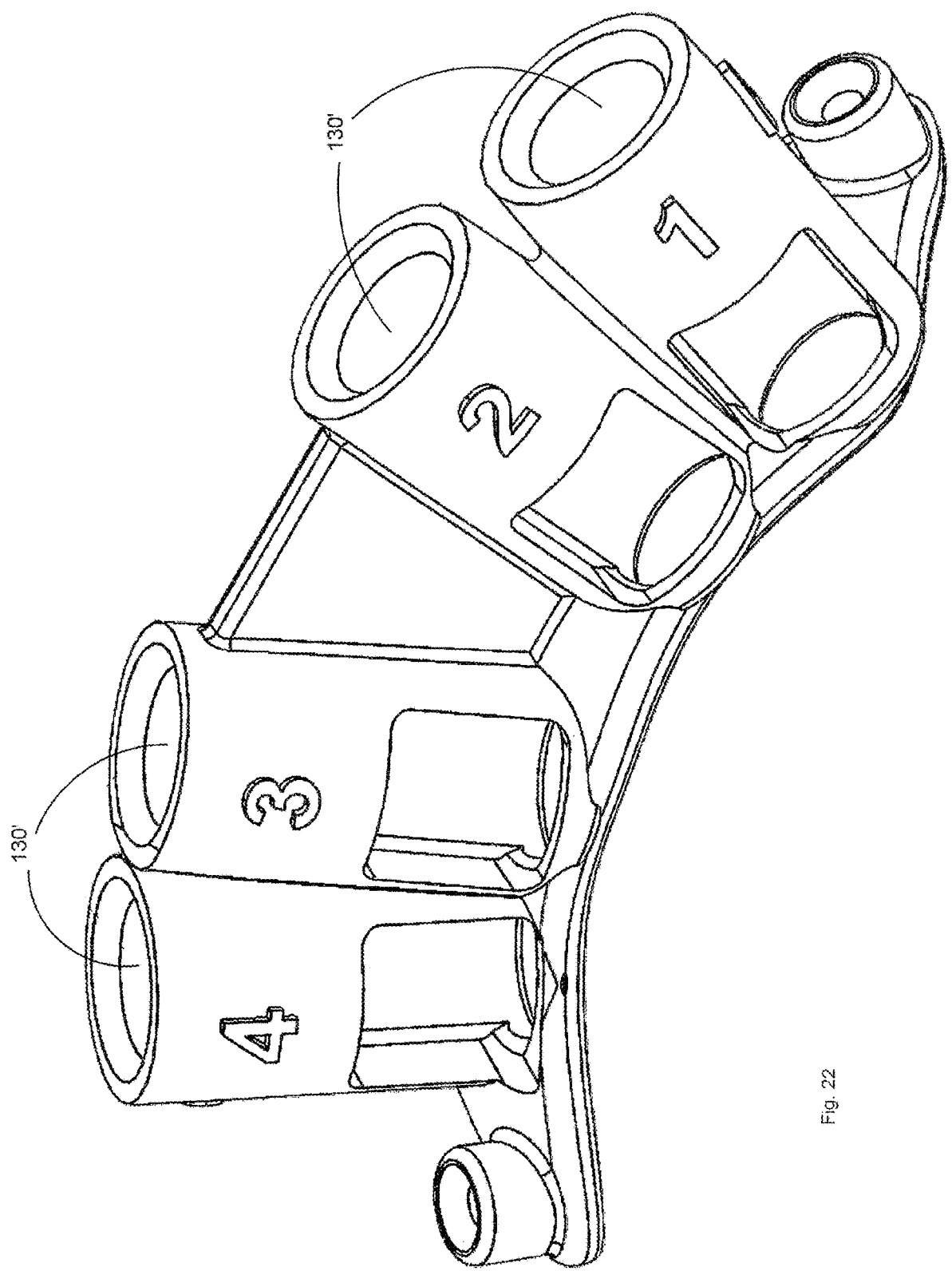
Figure 23:
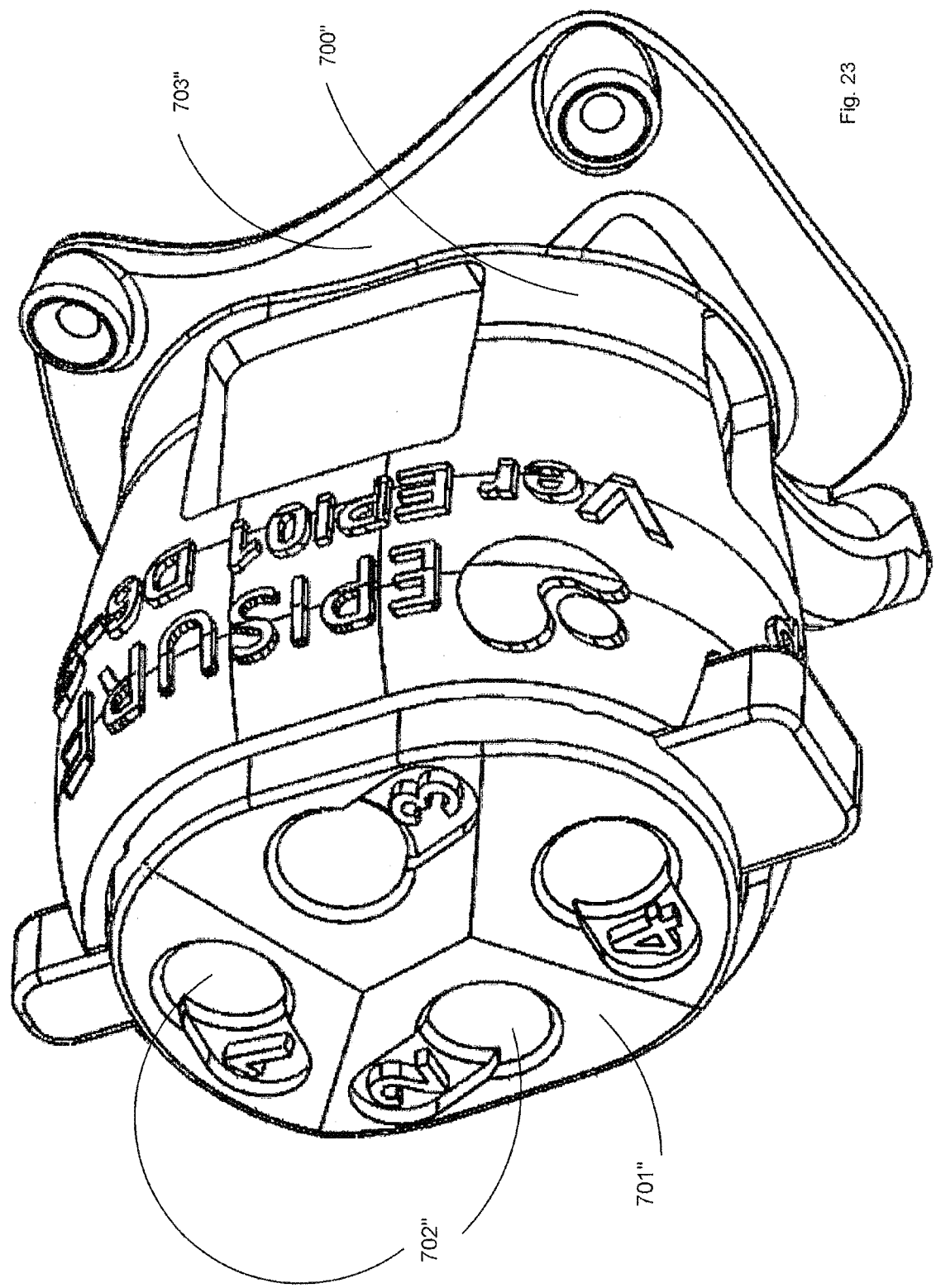
FIGS. 23 and 24 show two different perspective views of a complete transfer guide tool similar to that shown in FIGS. 7 and 8, but with four transfer guide channels.
Figure 24:
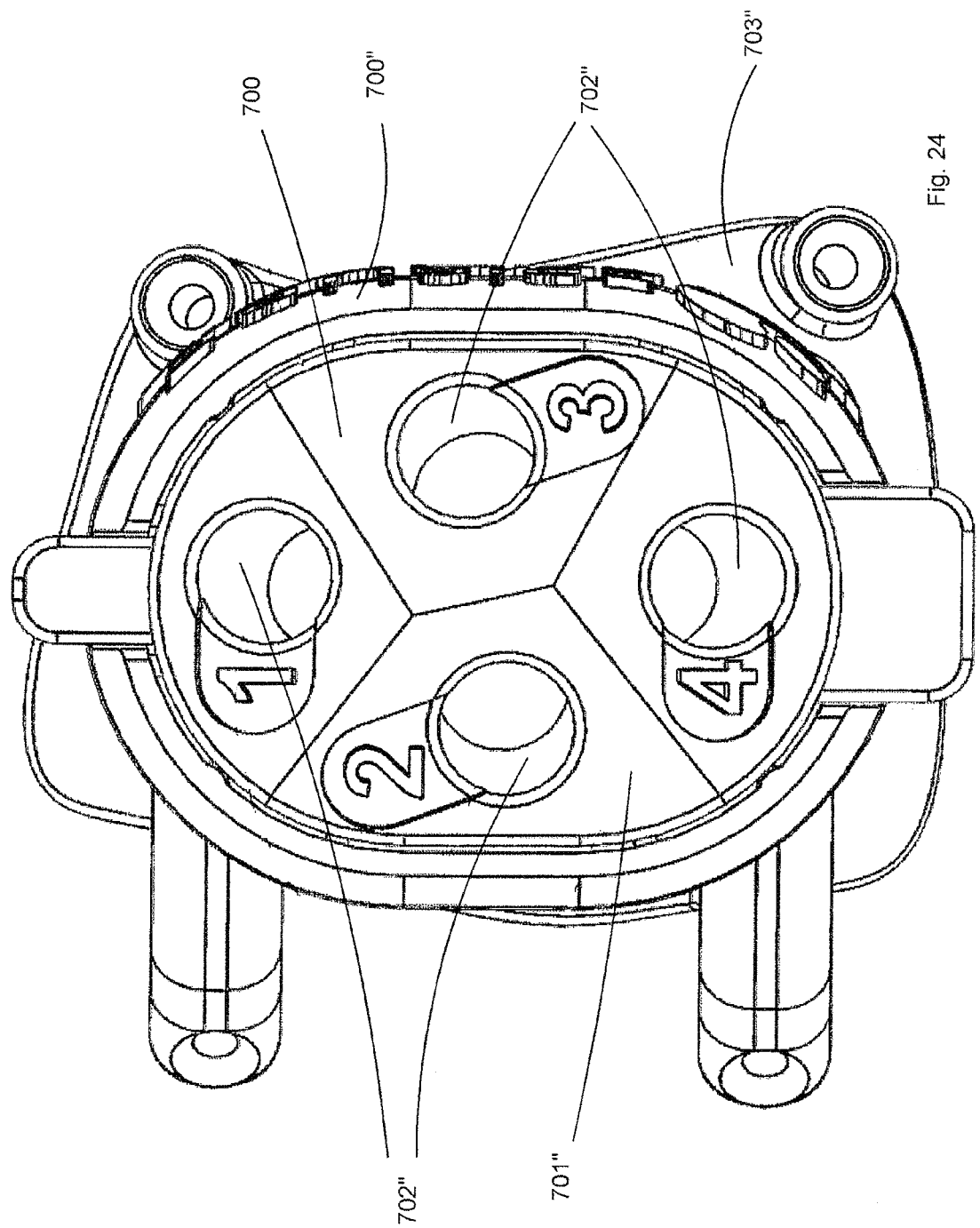
Figure 25:
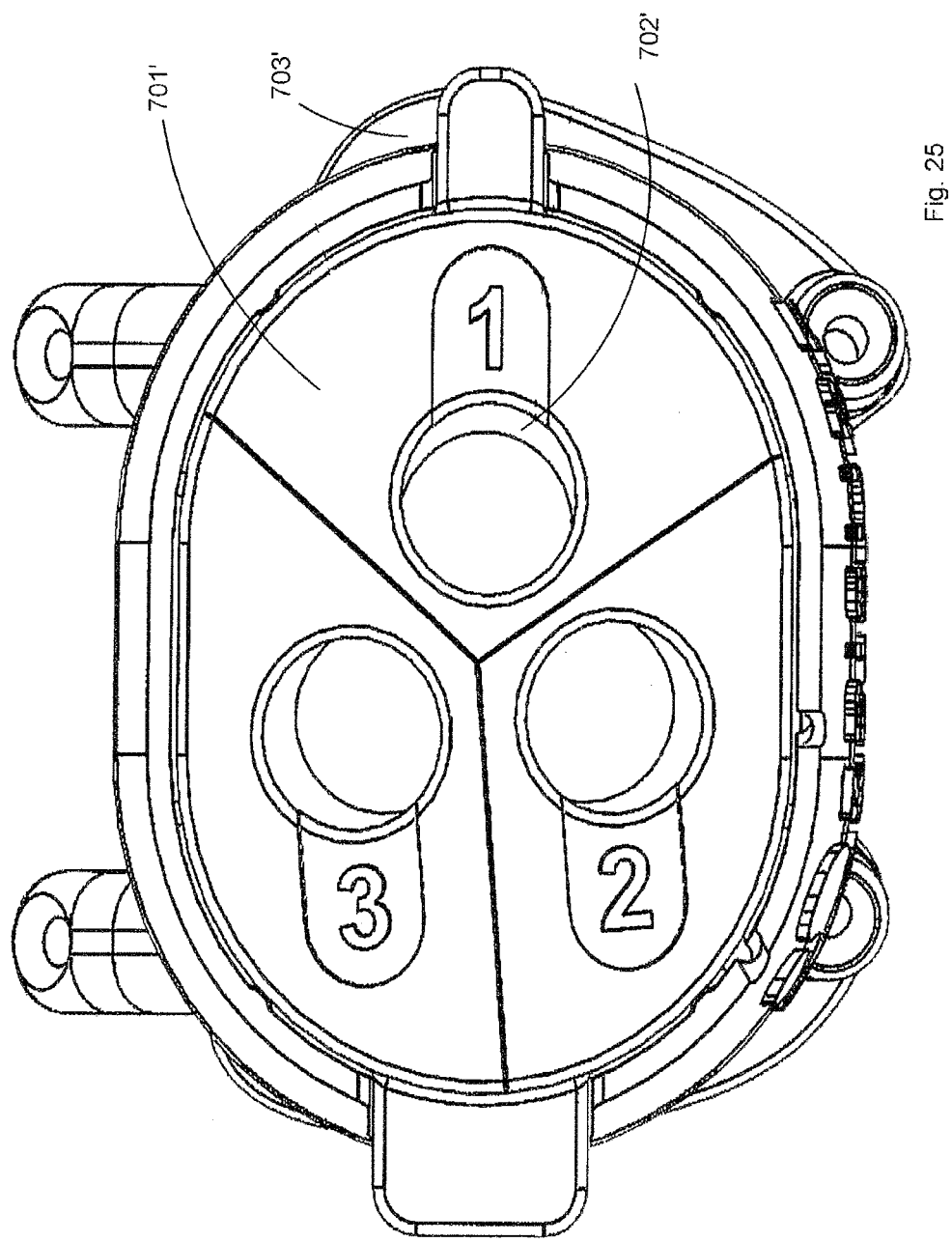
FIG. 25 shows another embodiment of a transfer guide tool with three transfer guide channels.
Figure 26:
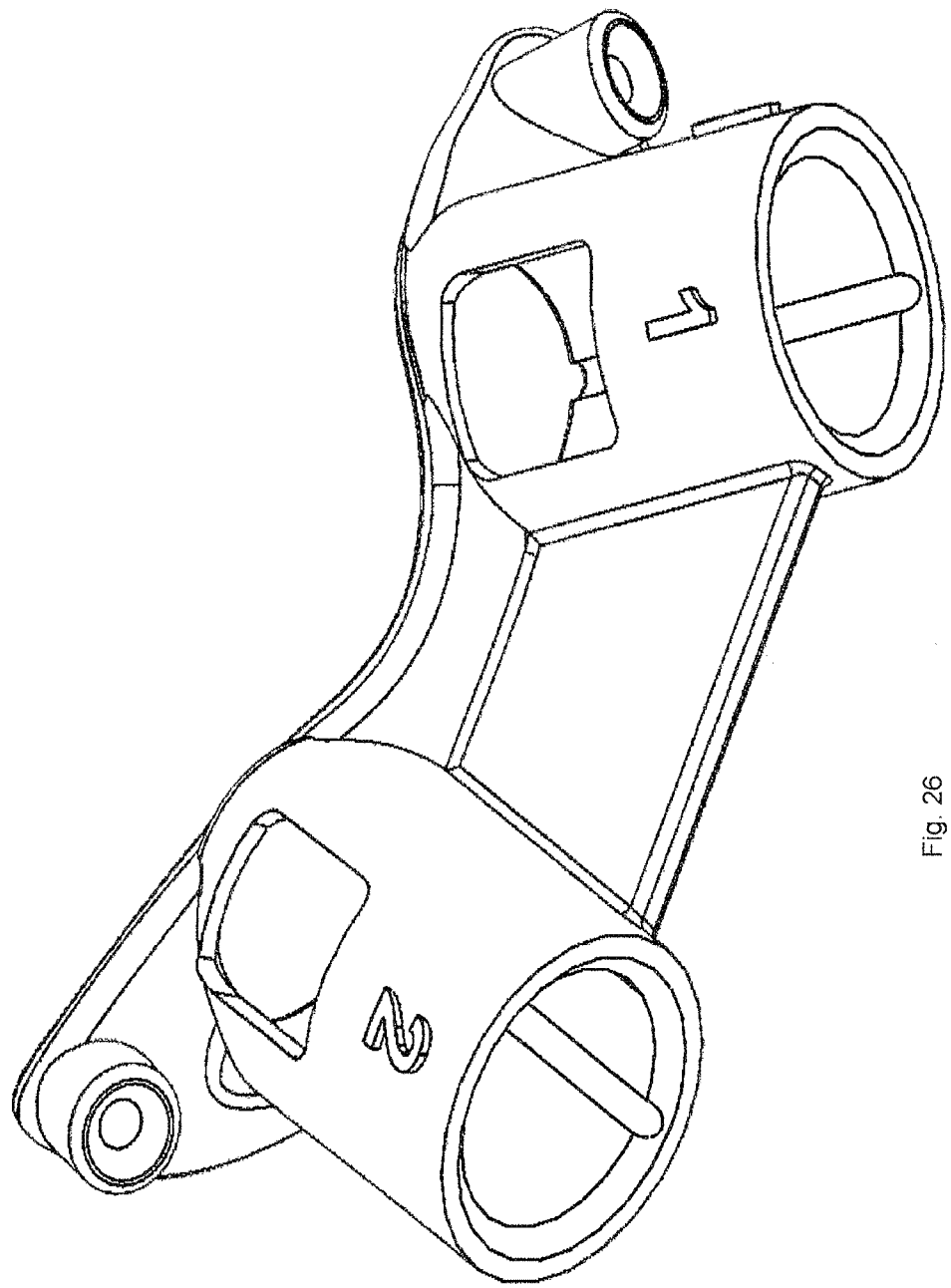
FIG. 26 shows a harvesting guide tool having only two guide channels.
Figure 27:
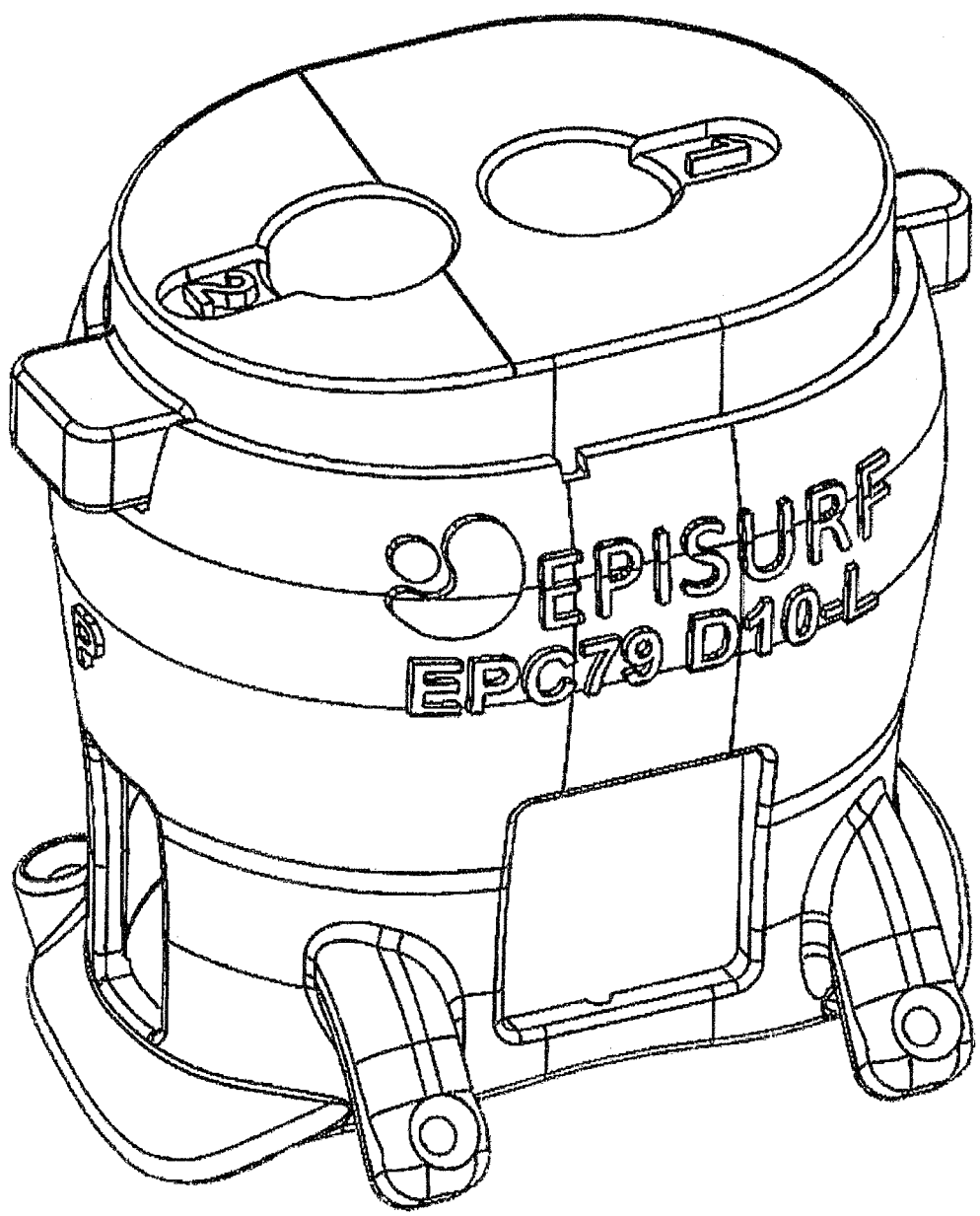
FIG. 27 shows a complete transfer guide tool with only two transfer guide channels.

FIGS. 21 and 22 show a version of a harvesting guide tool 100' with four channels 130', but which functions in the same way as that described above.

Figure 4:
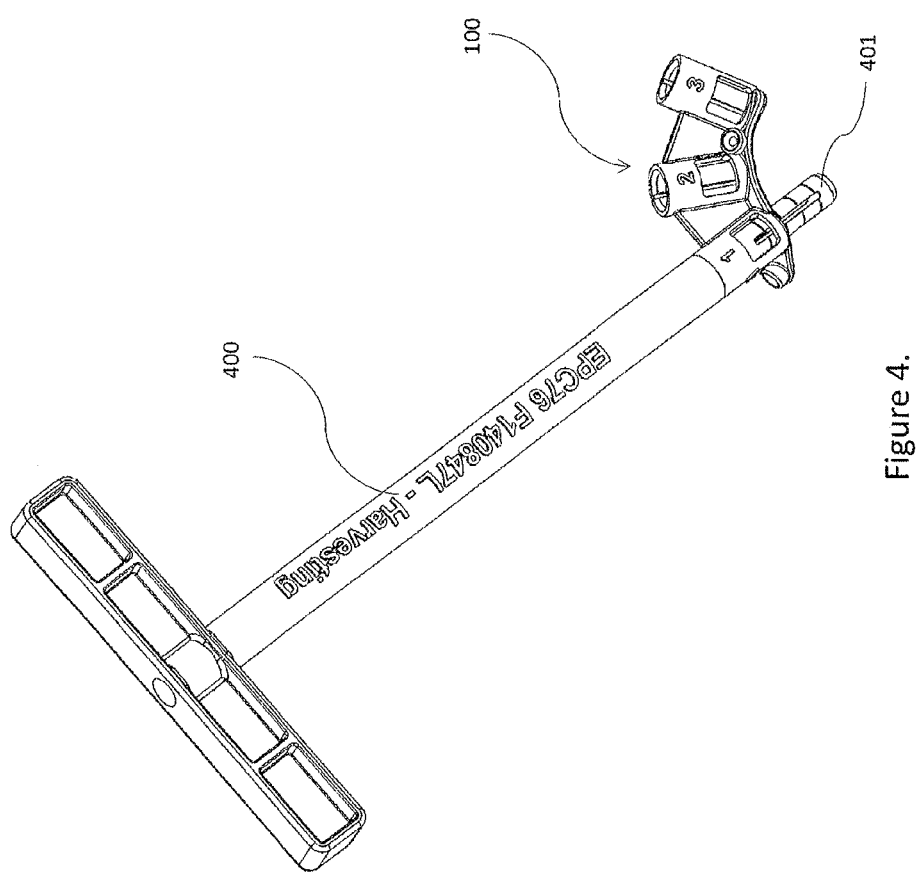
FIGS. 4, 5 and 6 show a plug harvesting tool and illustrate its use in the harvesting tool guide.

FIG. 4 shows an example of a tubular harvesting tool with a handle 400 and a harvesting guide 401. The combination of the harvesting tool 100 and the harvesting guide 401 makes it possible to harvest plugs of a certain depth/height.

Figure 5:
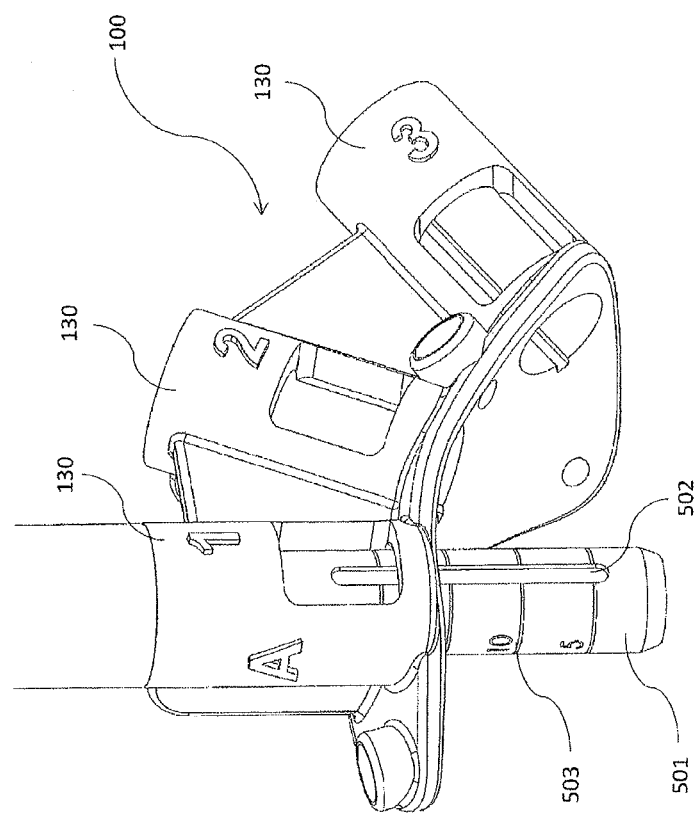

FIG. 5 shows an example of a harvesting guide tool 100 with three guide channels 130. Further, a cylindrical harvesting tool 501 is shown. The harvesting tool 501 has a measuring scale 503 indicating how deep into the bone the harvesting tool 501 has been inserted. The narrow window 502 on the harvesting tool 501 shows the plug inside the harvesting tool 501.

Figure 6:
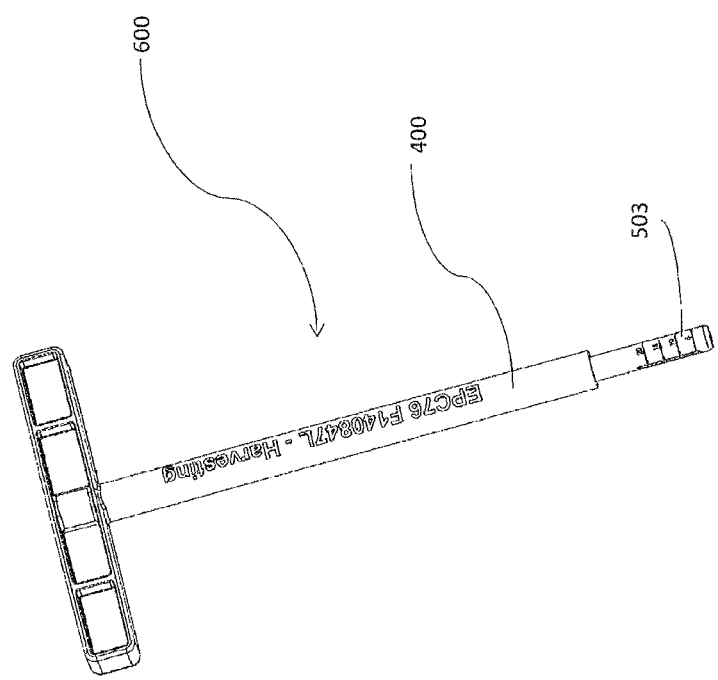

FIG. 6 shows an example of a harvesting tool 600 with a handle 400 and a measuring scale 503.

A guide tool 200 for insertion of one or more osteochondral plugs for osteochondral transplantation surgery in a joint 50 will now be described.

Figure 7:
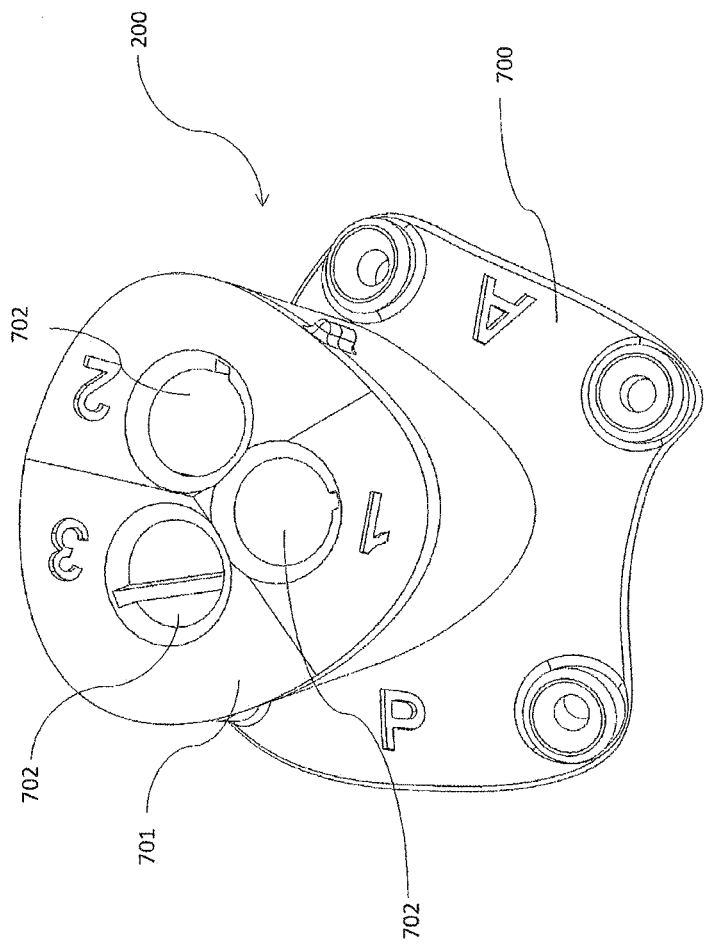
FIGS. 7 and 8 show two views of one embodiment of a transfer guide tool.
Figure 8:
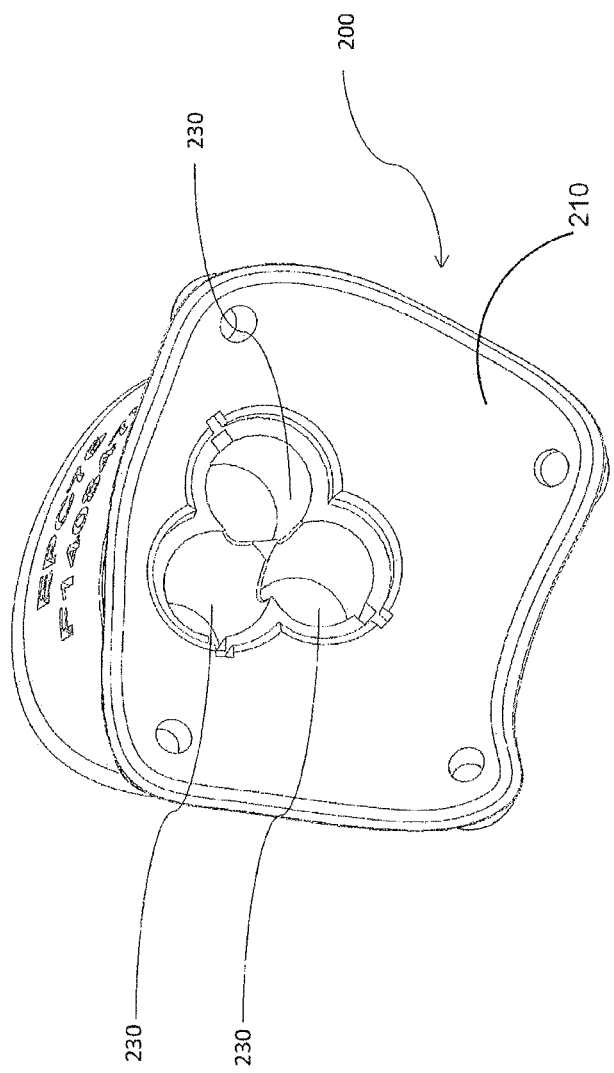

FIG. 7 shows an example of a transfer guide tool 200 comprising both a base part 700 and an inset part 701. FIG. 8 shows the same exemplified transfer guide tool 200 as in FIG. 7 with three guide channels 230 from another perspective showing an exemplified pattern of a plug formation.

The inset 701 has three channels 702 for guiding the making of three sockets. The base part 700 is labelled "A" and "P" to show the anterior and posterior directions of the transfer guide tool to facilitate correct position and placement. The inset 701 is provided with numerals 1, 2 and 3 to facilitate keeping track of plugs. The guide tool 200 comprises a cartilage contact surface 210 adapted to follow the shape of a surface of a cartilage or subchondral bone in a joint 50 into which surface the one or more osteochondral plugs are to be inserted, whereby the cartilage contact surface 210 and the surface of the cartilage or subchondral bone conform to each other. The guide tool 200 further comprises one or more guide channels 230 adapted to receive a respective insertion surgical tool, which slides within the guide channel 230, and is supported by the guide channel during insertion surgery. The transfer guide tool may further comprise a plurality of guide channels for insertion of a plurality of osteochondral plugs. The plurality of guide channels and the respective surgical tool may be of different sizes, whereby the plurality of inserted osteochondral plugs will be of different sizes. The guide tool may be provided with a stop function adapted to interact with a corresponding stop member provided on the surgical tool. The transfer guide tool may further comprise one or more detachably attached guide channel liners adapted to fit inside the one or more guide channels, and adapted to receive a respective surgical tool, by which tool a cylinder of cartilage and bone matter is removed from the damage site. The one or more guide channels may be adapted to position the one or more osteochondral plugs at a predetermined angle of rotation. The transfer guide tool 200 may guide preparation of the lesion site in a joint 50 before placement of one or more repair objects into the damaged site. A repair object should for example be a healthy cartilage and bone plug, but it might also conceivably be an implant. Preparation of the repair object site may for example be done using a drill bit which is guided to make a bores at certain angles into the bone at the site for the cartilage damage. The hole may also be made by for example a tubular body with teeth or a straight cutting edge. Prepared holes in the bone are used for the placement of cartilage and bone repair objects. A transfer guide tool 200 according to embodiments herein may be used together with different insertion tools for example a cartilage harvesting and insert tool for guiding the placement of healthy cartilage plugs replacing damaged bone and/or cartilage in a joint 50. The transfer guide tool 200 according to embodiments herein may also be used together with other insert tools for example an adapter or funnel.

The transfer guide tool 200 of embodiments herein can guide both the preparation of the repair site such as a hole making, and the insertion of the repair object into the hole. To serve this double purpose, the transfer guide tool 200 may consist of two different parts, as described above. The transfer guide tool 200 may have one base part conforming to an articular surface of a joint 50. Further, the transfer guide tool 200 may be provided with an inset which is arranged to be releasable from the base part. The transfer guide tool 200 according to embodiments herein, may be equipped with a positioning body comprising a cartilage contact surface and a guide body. The guide body may further be divided into two parts; a base part that stays on the positioning body and an inset. The inset comprises at least one guide channel. The at least one guide channel is designed to fit insert tools used inside the guide tool, for example a socket preparation tool or a plug insertion tool. The transfer guide tool 200 may also be used to guide other surgical tools or insert tools within the guide channels of the inset of the guide tool.

According to one preferred cartilage-and-bone plug harvesting and implantation method, the inset 701,701', 701", 1000, 1100, 1400 or 1500, with guide channels 230,701'or 702" is used for punch removal or drilling out, using the hole maker removal tool shown in FIG. 8a, of a single hole in the diseased condylar area through the appropriate guide channel, whereafter the inset is removed and the harvested plug is inserted into place with the inset removed and the hollow base part remaining in place. Then the inset is replaced and the next hole is made using the next guide channel, possibly removing a small portion of the just inserted healthy plug. Sequential hole-making/plug insertion makes it possible to have overlapping holes and plugs to better cover the diseased area.

FIG. 8A shows various views of one embodiment of a tool for making insertion holes by removal of damaged cartilage and bone.

Figure 9:
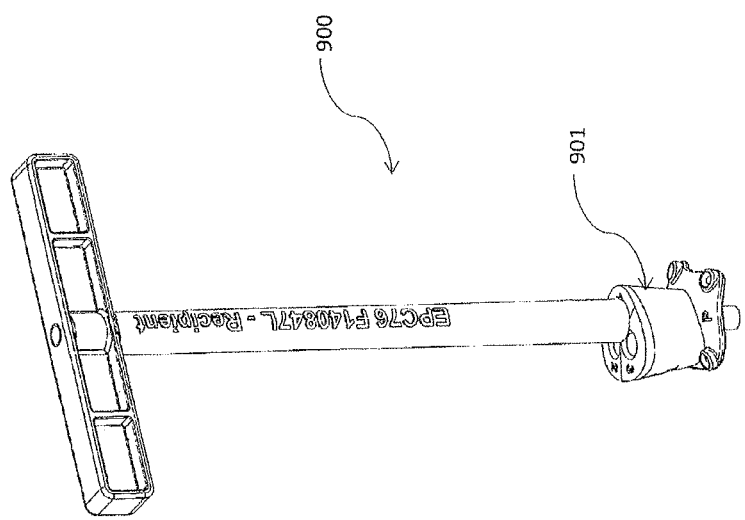
FIG. 9 shows the hole-maker removal tool engaged in the transfer guide tool.

FIG. 9 shows an example of a removal tool 900 mounted in a transfer guide 901 for making insertion holes.

Figure 10:
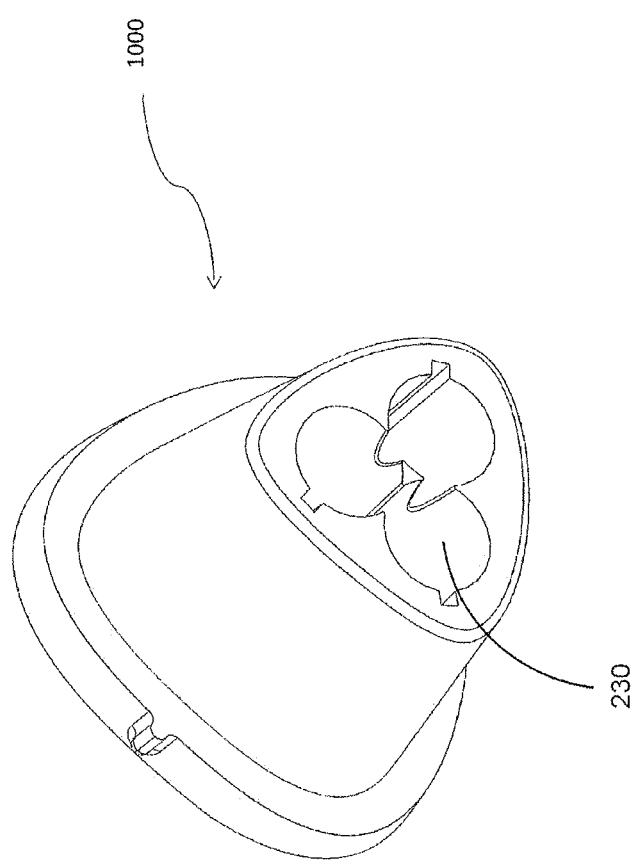
FIGS. 10 and 11 show two views of one embodiment of the inset of transfer guide tool.
Figure 11:
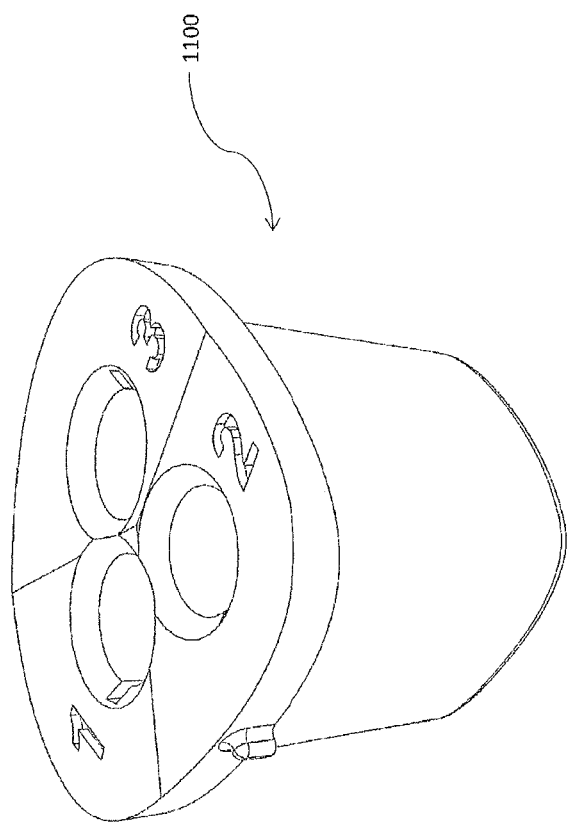

FIG. 10 shows an example of three-holed inset 1000 of a transfer guide tool 200 and FIG. 11 shows another exemplified three-holed inset 1100 of a transfer guide tool 200.

Figure 12:
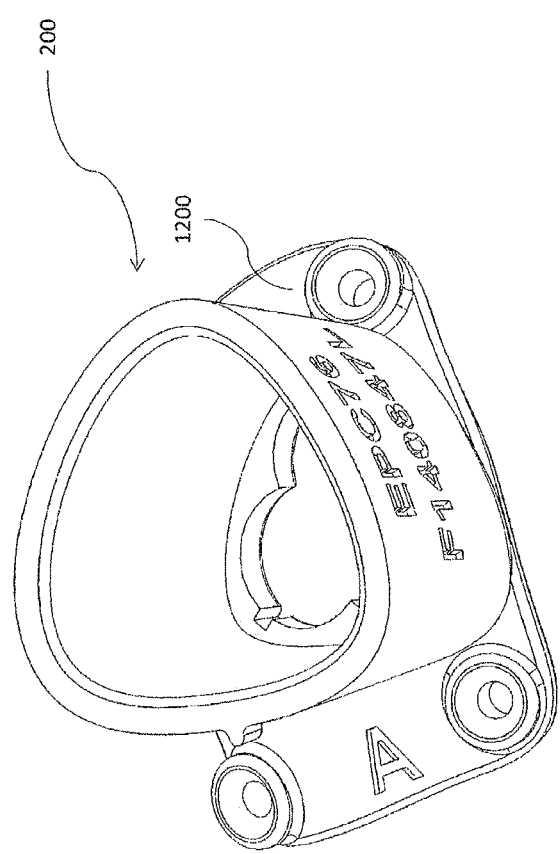
FIGS. 12 and 13 show two views of an example of a socket base of a transfer guide tool according to embodiments herein.
Figure 13:
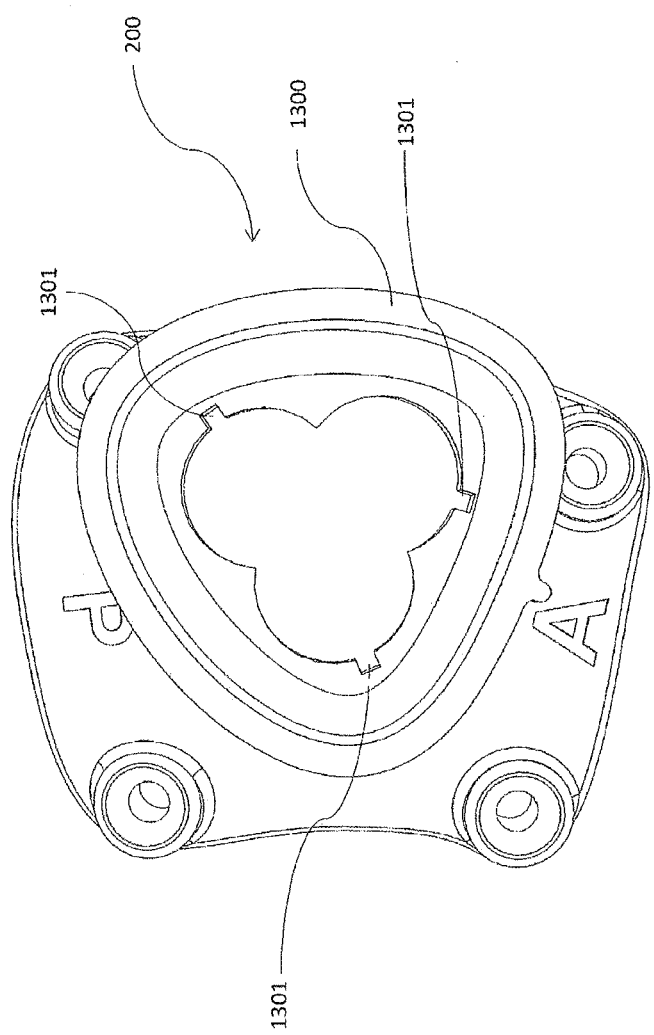

FIGS. 12 and 13 shows an example of the base part 1200 of a transfer guide tool 200 from two different perspectives.

Figure 14:
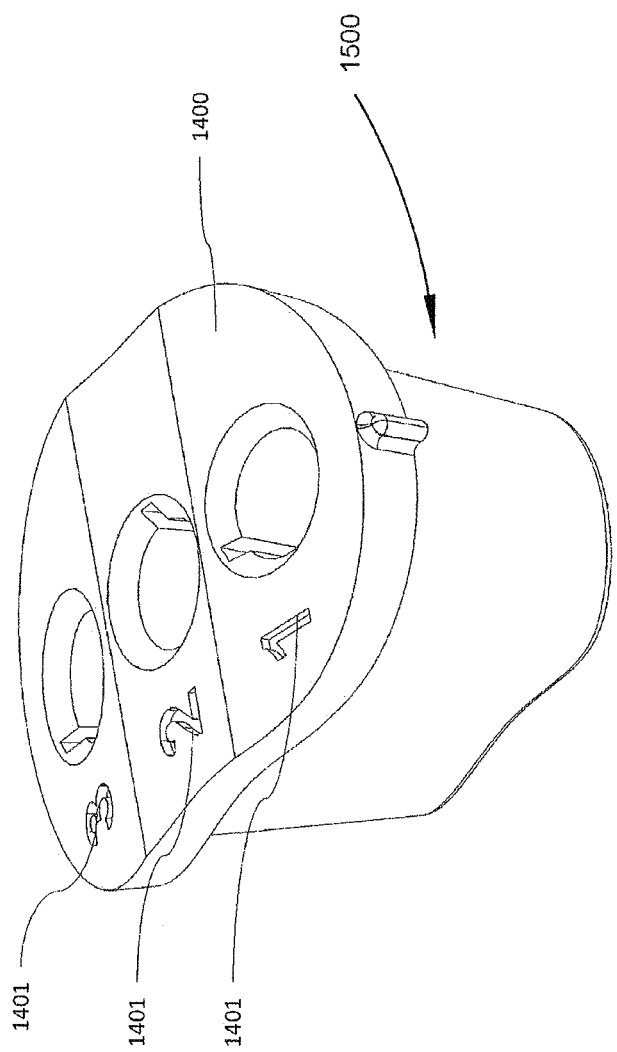
FIG. 14 shows another example of an inset for a transfer guide tool according to embodiments herein.

FIG. 14 shows an example of an inset 1500 of a transfer guide tool, with numerals 1401 showing where to place which repair object, or plug. The inset 1500 may have one or more channels to guide the hole preparation. The transfer guide tool used together with specific tools for creation of the insertion hole at the damaged site may have a function that adjusts the depth of the hole so a desired depth is obtained. In one exemplified embodiment of embodiments herein, the tool that creates the insertion hole has a handle that matches the transfer guide tool and creates a stop function so the desired depth of the insertion hole is obtained.

The base part of the transfer guide will then during the insertion phase guide the insertion of the repair object and provide stability during the insertion phase. The transfer guide can also guide the insertion so that the desired rotation of the inserted plug is obtained. The inset of the transfer guide tool can, in certain procedures, be removed when an insertion hole has been created and the plug is to be inserted.

Figure 15:
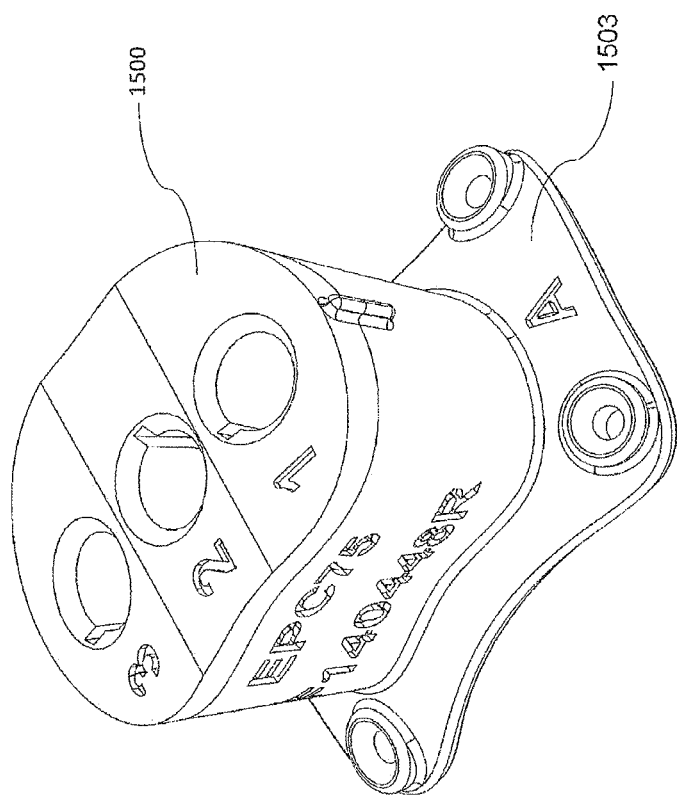
FIG. 15 shows an example of a transfer guide tool with both an inset and a socket base engaged with each other according to embodiments herein.
Figure 16:
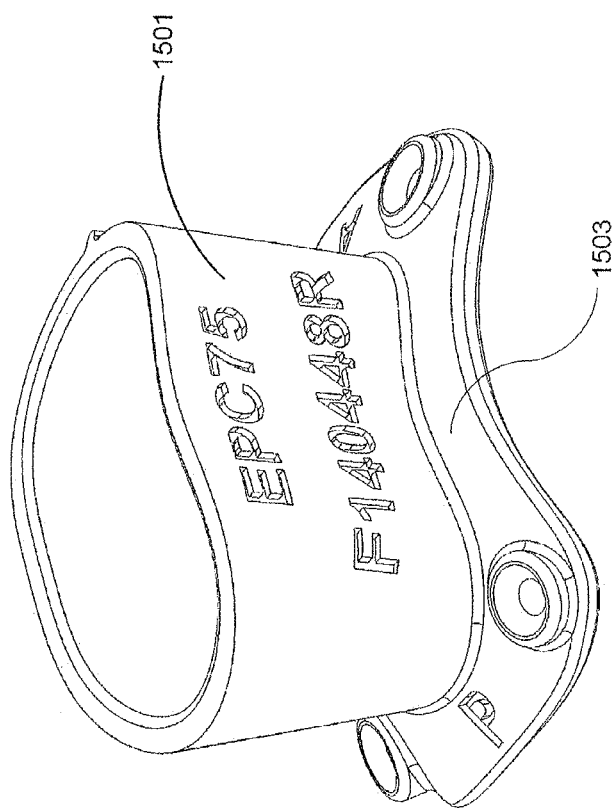
FIGS. 16 and 17 are two different views of the socket base of the transfer guide tool of FIG. 15.
Figure 17:
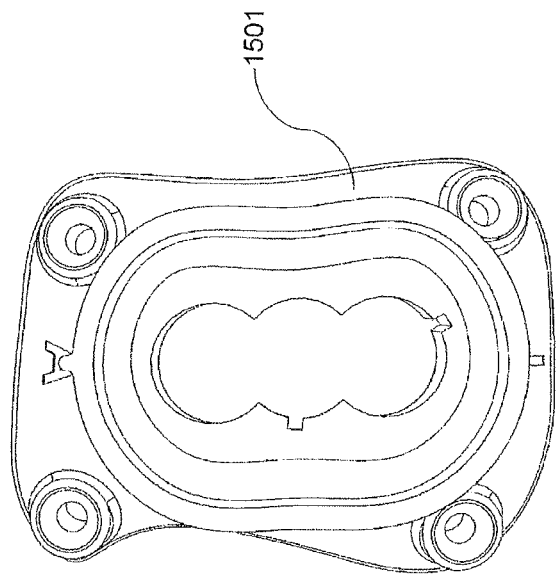

FIG. 15 shows yet another example of a transfer guide tool with both an insert 1500 and base part 1501 in place. FIG. 16 shows the base part 1501 alone and FIG. 17 shows in from above.

Figure 18:
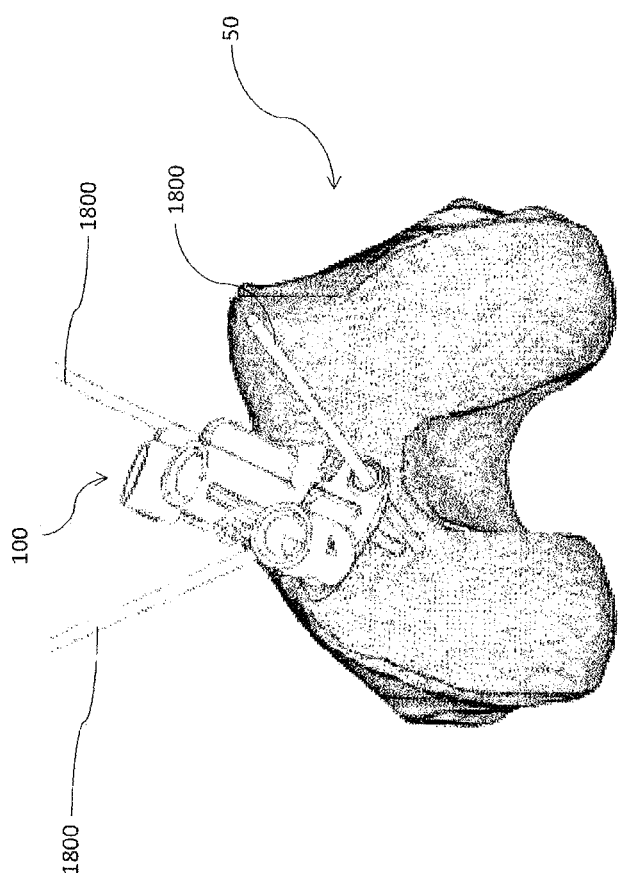
FIG. 18 shows an example of a harvesting guide tool according to embodiments herein placed on a medial condyle of a left femur.

FIG. 18 shows an example of a harvesting guide tool 100 placed on the left medial femoral condyle of the distal end of the femur 50, i.e. of the knee joint. The guide tool 100 is fastened to the bone with surgical pins 1800.

Figure 19:
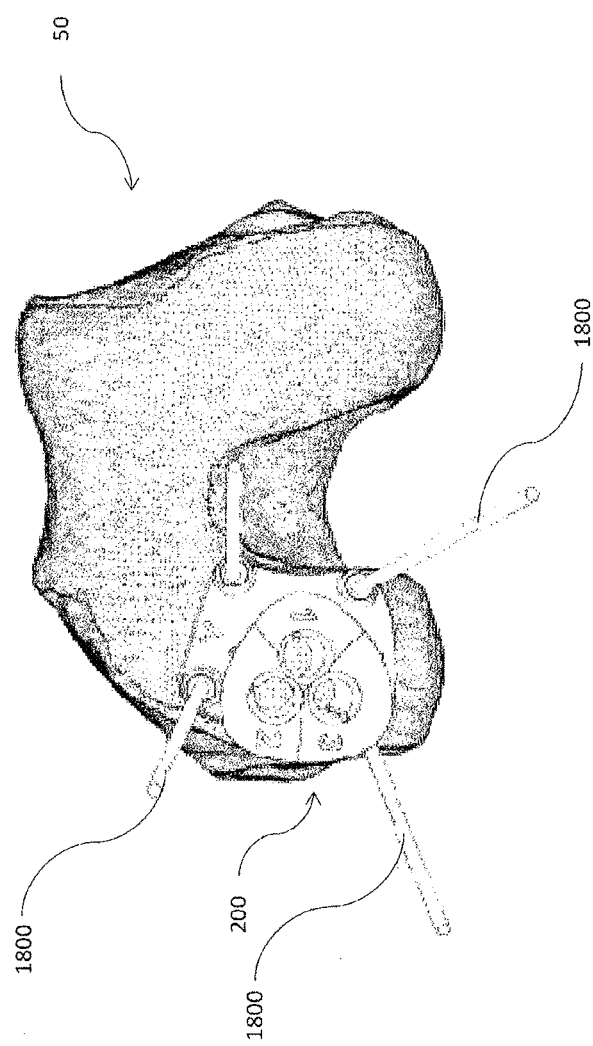
FIG. 19 shows an example of a transfer guide tool according to embodiments herein placed on the medial condyle of a left femur.

FIG. 19 shows an example of a transfer guide tool 200 placed on the left medial femora condyle, i.e. of the knee joint. The guide is fastened to the bone with surgical pins 1800.

Proper pre-operative planning before performing an osteochondral transfer has several advantages. If a lesion is thoroughly assessed by the aid of MR or CT data, the surgeon can be very well prepared. Planning of where the plugs can be harvested, planning of what pattern and what sizes of plugs that shall be applied as well as matching of the curvature of the harvested plugs and the curvature of the lesion site may reduce the risks of unsuccessful outcomes of these kinds of procedures. A method of designing a system for performing osteochondral transplantation surgery in a joint 50 will now be described. The system comprises a harvesting guide tool, one or more osteochondral plugs, and a transfer guide tool for insertion of the one or more osteochondral plugs in a cartilage damage site on an articular surface of the joint 50. The method comprises determining physical parameters for the cartilage damage site in the joint 50 based on obtained image data, generating, based on the determined physical parameters, design parameters for the one or more osteochondral plugs to fit the cartilage damage site, wherein the design parameters comprise at least the number of, the size of, and the relative placement of, the one or more osteochondral plugs, selecting, based on the determined physical parameters, at least one healthy surface of the joint 50 substantially aligning with the surface of the cartilage damage site, from at least one healthy surface the one or more osteochondral plugs is to be harvested, generating, based on the generated design parameters for the one or more osteochondral plugs, design parameters for each of the respective guide tools. The harvesting guide tool and the transfer guide tool 200 may thus be designed using a design system wherein a knee with the articular lesion is examined using a technique such as MR or CT and analyzed and processed in a computer and wherein the collected data is further processed and used in the design of the guide tools.

Figure 20:
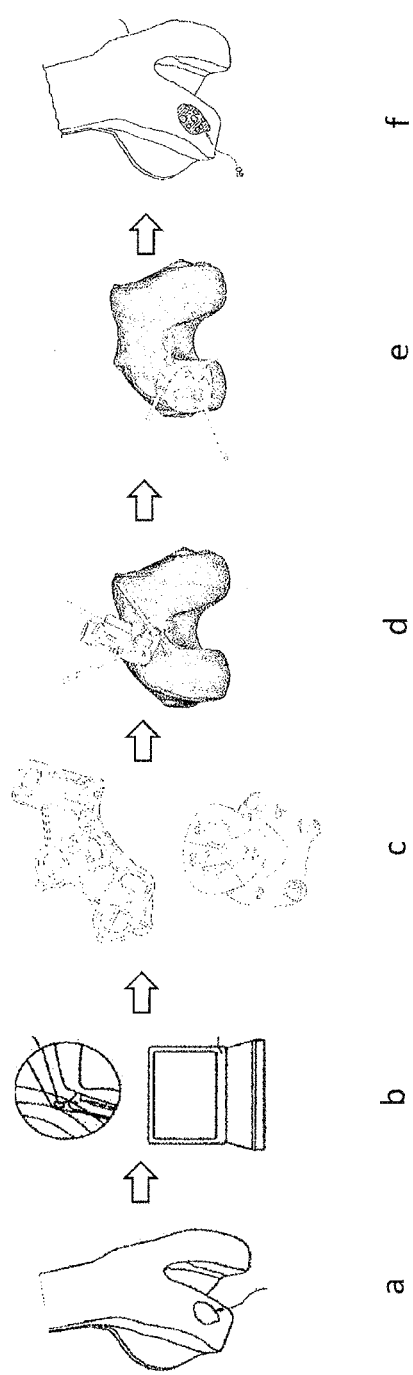
FIG. 20 shows a schematic representation of methods described herein.

FIG. 20 is a schematic representation of an exemplified process;

a) A schematic drawing of a distal end of the left femur showing a lesion on the medial condyle.

b) A MR scan is performed on the knee. The MR data is processed leading to a virtual 3D model of the knee and a damage assessment presenting the bone and/or cartilage lesion. The MR scan also assures that there is healthy un-loaded cartilage and bone material accessible for harvesting during the operation, typically the condylar surface near or behind the patella.

c) Based on the spreading and characteristics of the lesion and the anatomy of the patient, a pattern of one or more cylindrical plugs on the lesion site is planned. One guide for harvesting of bone and cartilage plugs is designed and produced, and one guide for insertion of bone and cartilage plugs is designed and produced. The harvesting guide can be designed to make sure that each harvested plug is extracted normal to the condylar surface, thereby assuring that the plug, when inserted will have a top surface flush with the condylar surface being repaired. In specific cases, the harvesting guide can be designed to harvest a plug with an oblique surface to match a specific planned surface and hole in the diseased condylar surface.

d) A harvesting guide is placed on a non-weight-bearing area of the femur, and fastened to the bone with surgical pins. A harvesting tool is used together with the guide to remove cartilage and bone plugs for transplantation. The harvesting tool can be of standard design or can be a specific tool matching the harvesting guide. In the latter case, the tool can be designed so that there is a stop function giving the plug an exact length. After harvesting of one or more plugs, the harvesting guide is removed. The plugs may be marked with a rotation mark during the harvesting process to give desired rotation of the plug through rotation mark matching in the insertion step.

e) A transfer guide is placed in the area of the lesion on the femur to guide the insertion of plugs in a pre-determined pattern on the lesion site. The transfer guide has two parts, a base that is fastened to the bone with surgical pins and a removable insert. The insert has one or more channels to guide the insertion tool for excavation of the one or more socket on the lesion site, where cartilage and bone plugs will be inserted. One hole is created with the help of the insertion tool that is guided by the transfer guide with the inset in place. The insertion tool can be of standard design or can be a specific tool matching the transfer guide. In the latter case, the tool can be designed so that there is a stop function giving the hole an exact depth. The guide insert is thereafter removed. After checking that the socket depth is correct or possible adjustment of the socket depth or plug length, the plug is inserted. If several plugs are inserted, the guide insert is put back in place after insertion of the first plug and the procedure is repeated until all plugs have been inserted. This makes it possible to have overlapping plugs, with preceding plugs being cut into by the hole maker. The transfer guide is thereafter totally removed.

f) A schematic drawing of a femoral condyle showing a lesion site after cartilage and bone plugs have been inserted. The plugs may cover the whole lesion or the main part of the surface area of the lesion.

The plugs mentioned herein may be of any suitable size. As an example, they may be 4-10 mm in diameter, and as a further example up to 12 mm in diameter. The length of the plugs may for example be twice the diameter. As an example, the plugs may have a length of 10-20 mm, and, as another example the may be up of any length up to 25 mm. When a plurality of plugs is used in a damage site, as an example 2-5 plugs may be used. As another example, any number up to 10 plugs may be used for a damage site. When a large number of plugs are used, at least some of the plugs may be of smaller diameter. The plugs may cover any part of the damage site. As an example the plugs may cover at least 70% of the damage site.

The examples and embodiments mentioned herein may be applied for any joint of the body.

The foregoing disclosure is not intended to be limited to embodiments herein to the precise forms or particular fields of use as disclosed. It is contemplated that various alternate embodiments and/or modifications to embodiments herein, whether explicitly described or implied herein, are possible in light of the disclosure. Accordingly, the scope herein is defined only by the claims.

The invention claimed is:

1. A system for performing osteochondral transplantation surgery in a joint; the system comprising;
   a harvesting guide tool for harvesting one or more osteochondral plugs;
   a transfer guide tool for insertion of said one or more osteochondral plugs in a damage site on an articular surface of the joint;
   wherein each respective guide tool is provided with a cartilage contact surface adapted to follow a respective harvesting site surface or a damage site surface of a cartilage or subchondral bone in a joint respectively, whereby each respective cartilage contact surface is adapted to conform to said respective site surface, and
   wherein each respective guide tool comprises one or more guide channels adapted to receive a respective surgical tool such that the respective surgical tool slides within the guide channel, and is supported by the guide channel.

2. The system according to claim 1, wherein each respective guide tool comprises a plurality of guide channels, respectively for harvesting and for insertion of a plurality of osteochondral plugs.

3. The system according to claim 2, wherein the plurality of guide channels and the respective surgical tools are configured to harvest and insert a plurality of osteochondral plugs of different sizes.

4. The system according to claim 2, wherein said transfer guide tool is adapted for insertion of said plurality of osteochondral plugs in a predetermined pattern and orientation, whereby a surface curvature of each inserted osteochondral plug substantially corresponds to an original articular surface curvature at the damage site, prior to damage.

5. The system according to claim 1, wherein each respective guide tool is individually designed based on patient specific data.

6. The system according to claim 1, wherein each respective guide tool is provided with pin-holes for fastening each respective guide tool to each respective surface of the cartilage or subchondral bone.

7. The system according to claim 1, wherein each respective guide tool is provided with a stop function adapted to interact with a corresponding stop member provided on each respective surgical tool.

8. A harvesting guide tool for harvesting one or more osteochondral plugs for osteochondral transplantation surgery in a joint; the harvesting guide tool comprising:
   a cartilage contact surface adapted to follow a shape of a harvesting site surface of a cartilage or subchondral bone in a joint from which site surface the one or more osteochondral plug is to be harvested, whereby said cartilage contact surface is adapted to conform to the site surface, and
   one or more guide channels adapted to receive a respective harvesting surgical tool such that a respective harvesting surgical tool slides into one of the guide channels, and is supported by the one of the guide channels during harvesting surgery.

9. The harvesting guide tool according to claim 8, further comprising a plurality of guide channels for harvesting a plurality of osteochondral plugs, wherein interiors of said guide channels are provided with marking means for marking a rotational position of harvested plugs.

10. The harvesting guide tool according to claim 9, wherein the plurality of guide channels corresponds to a plurality of respective harvesting surgical tools of various sizes, thereby enabling a plurality of harvested osteochondral plugs to be of various sizes.

11. The harvesting guide tool according to claim 8, wherein said guide tool is individually designed based on patient specific data.

12. The harvesting guide tool according to claim 8, wherein said guide tool is provided with pin-holes for fastening said guide tool to the surface of the cartilage or subchondral bone.

13. The harvesting guide tool according to claim 8, wherein said guide tool is provided with a stop function adapted to interact with a corresponding stop member provided on said harvesting surgical tool.

14. A transfer guide tool for transfer of one or more osteochondral plugs for osteochondral transplantation surgery in a joint; the guide tool comprising:
   a cartilage contact surface adapted to follow a damage site surface of a cartilage or subchondral bone in a joint into which surface the one or more osteochondral plugs are to be inserted, whereby said cartilage contact surface is adapted to conform to the damage site surface, and
   one or more guide channels adapted to receive a respective hole making surgical tool such that the respective hole making surgical tool slides within one of the guide channels, and is supported by the one of the guide channels during surgery.

15. The transfer guide tool according to claim 14, further comprising a plurality of guide channels for insertion of a plurality of osteochondral plugs using insertion surgical tools.

16. The transfer guide tool according to claim 15, wherein the plurality of guide channels corresponds to a plurality of respective surgical tools of various sizes, thereby enabling a plurality of inserted osteochondral plugs to be of different sizes.

17. The transfer guide tool according to claim 14, wherein said guide tool is individually designed based on patient specific data.

18. The transfer guide tool according to claim 14, wherein said guide tool is provided with pin-holes configured for fastening said guide tool to the surface of the cartilage or subchondral bone.

19. The transfer guide tool according to claim 14, wherein said transfer guide tool is provided with a stop function adapted to interact with a corresponding stop member provided on said hole making or an insertion surgical tool.

20. The transfer guide tool according to claim 14, further comprising one or more detachably attached guide channel inserts adapted to fit inside the one or more guide channels, and adapted to receive a respective surgical tool.

21. The transfer guide tool according to claim 14, wherein said one or more guide channels are adapted to position said one or more osteochondral plugs at a predetermined angle of rotation.

22. The transfer guide tool according to claim 14, wherein the transfer guide tool comprises:
 a) a base portion; and
 b) a removable inset having guide channels and being housed in said base portion.

23. The transfer guide tool according to claim 22, wherein said base portion has a bottom portion adapted to conform to a condylar area or a trochleal area of a femoral knee.

24. A method of designing a system for performing osteochondral transplantation surgery in a joint; the system comprising:
 a first guide tool for harvesting one or more osteochondral plugs; and
 a second guide tool for transfer of said one or more osteochondral plugs to a damage site on an articular surface of the joint;
 the method comprising:
 receiving radiology image data representing one or more images of said joint,
 determining physical parameters for the damage site in the joint based on said received image data,
 generating, based on said determined physical parameters, design parameters for said one or more osteochondral plugs to fit the damage site, wherein the design parameters comprise at least a number of, a size of and a relative placement of said one or more osteochondral plugs,
 selecting, based on said determined physical parameters, at least one healthy surface of the joint, having a shape at least in part following of the surface of said damage site as it was prior to damage, from which at least one healthy surface said one or more osteochondral plugs are to be harvested, and
 generating, based on the generated design parameters for said one or more osteochondral plugs, design parameters for each respective guide tool.

* * * * *